United States Patent
Yang et al.

(10) Patent No.: US 7,989,469 B2
(45) Date of Patent: Aug. 2, 2011

(54) CERTAIN CHEMICAL ENTITIES, COMPOSITIONS, AND METHODS

(75) Inventors: Zhe Yang, Daly City, CA (US); Scott Collibee, San Carlos, CA (US); Alex R. Muci, San Francisco, CA (US); Jianchao Wang, Foster City, CA (US); Luke W. Ashcraft, San Francisco, CA (US); Jeff Gardina, Santa Clara, CA (US); Brian Stoltz, San Marino, CA (US); Gustave Bergnes, Pacifica, CA (US); Bradley P. Morgan, Moraga, CA (US)

(73) Assignee: Cytokinetics, Incorporated, South San Francisco, CA (US)

( * ) Notice: Subject to any disclaimer, the term of this patent is extended or adjusted under 35 U.S.C. 154(b) by 235 days.

(21) Appl. No.: 12/364,394

(22) Filed: Feb. 2, 2009

(65) Prior Publication Data

US 2009/0253737 A1    Oct. 8, 2009

Related U.S. Application Data

(60) Provisional application No. 61/026,067, filed on Feb. 4, 2008.

(51) Int. Cl.
*A61K 31/437* (2006.01)
*C07D 471/04* (2006.01)
*A61P 25/00* (2006.01)

(52) U.S. Cl. ........................... 514/303; 546/118
(58) Field of Classification Search .................. 514/303; 546/118
See application file for complete search history.

(56) References Cited

U.S. PATENT DOCUMENTS

| 7,279,580 | B2 | 10/2007 | Goodacre et al. |
| 7,598,248 | B2 | 10/2009 | Muci et al. |
| 7,851,484 | B2 | 12/2010 | Morgan et al. |
| 2004/0166137 | A1 | 8/2004 | Lackey |
| 2005/0197328 | A1 | 9/2005 | Bailey et al. |
| 2005/0250794 | A1 | 11/2005 | Napper et al. |
| 2006/0019952 | A1 | 1/2006 | Distefano et al. |
| 2006/0148805 | A1 | 7/2006 | Chen et al. |
| 2007/0197507 | A1 | 8/2007 | Morgan et al. |
| 2007/0275984 | A1 | 11/2007 | Imogai et al. |
| 2008/0096903 | A1 | 4/2008 | Chen et al. |
| 2009/0023724 | A1 | 1/2009 | Mortensen et al. |
| 2009/0029345 | A1 | 1/2009 | Russell et al. |
| 2009/0247571 | A1 | 10/2009 | Muci et al. |

FOREIGN PATENT DOCUMENTS

| WO | WO2005/108374 A1 | 11/2005 |
| WO | 2008075007 | * 6/2008 |
| WO | WO2010/068483 A2 | 6/2010 |

* cited by examiner

*Primary Examiner* — D Seaman
*Assistant Examiner* — Niloofar Rahmani
(74) *Attorney, Agent, or Firm* — Foley & Lardner LLP

(57) ABSTRACT

Provided are certain chemical entities, and methods of use to modulate skeletal myosin, skeletal actin, skeletal tropomyosin, skeletal troponin C, skeletal troponin I, skeletal troponin T, and skeletal muscle, including fragments and isoforms thereof, as well as the skeletal sarcomere, and methods of use in the treatment of neuromuscular disorders, conditions having muscle wasting, claudication, frailty, metabolic syndrome, muscle atrophy associated with disuse, and muscle fatigue, and other indications.

38 Claims, No Drawings

CERTAIN CHEMICAL ENTITIES, COMPOSITIONS, AND METHODS

This application claims the benefit of U.S. Provisional Patent Application No. 61/026,067, filed Feb. 4, 2008, which is incorporated herein by reference for all purposes.

Provided are certain chemical entities that modulate the contractility of the skeletal sarcomere. Also provided are certain chemical entities, pharmaceutical compositions and methods of treatment of one or more conditions or diseases, such as neuromuscular disorders (e.g., ALS), conditions having muscle wasting (e.g., sarcopenia and cachexia syndromes), claudication, frailty, metabolic syndrome, muscle atrophy associated with disuse, muscle fatigue, and other acute and chronic conditions and diseases.

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament (also $Ca^{2+}$ modulated) coupled with return of the catalytic domain and light chain to their starting conformation/orientation completes the contraction and relaxation cycle, responsible for intracellular movement and muscle contraction.

Tropomyosin and troponin mediate the calcium effect on the interaction on actin and myosin. The skeletal troponin complex regulates the action of several actin units at once, and is comprised of three polypeptide chains: skeletal troponin C, which binds calcium ions; troponin I, which binds to actin; and troponin T, which binds to tropomyosin.

Troponin, a complex of three polypeptides is an accessory protein that is closely associated with actin filaments in vertebrate muscle. The troponin complex, acts in conjunction with the muscle form of tropomyosin to mediate the Ca.2+ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin, inhibits the interaction of actin and myosin. Troponin C is capable of binding up to four calcium molecules. Studies suggest that when the level of calcium in the muscle is raised, troponin C causes troponin I to loose its hold on the actin molecule, causing the tropomyosin molecule shift, thereby exposing the myosin binding sites on actin and stimulating myosin ATPase activity.

Human skeletal muscle is composed of different types of contractile fiber, classified by their myosin type and termed either slow or fast fibers. Table 1 summarizes the different proteins that make up these types of muscle.

| | Muscle Fiber Type | |
|---|---|---|
| | Fast skeletal | Slow Skeletal |
| Myosin Heavy Chain | IIa, (IIb*), IIx/d | Cardiac β |
| Troponin I (TnI) | TnI fast SK | TnI slow SK |
| Troponin T (TnT) | TnT fast SK | TnT slow SK |
| Troponin C (TnC) | TnC fast SK | TnC slow/cardiac |
| Tropomyosin | TM-β/TM-α/TPM 3 | TM-β/TM-αs |

In healthy humans most skeletal muscles are composed of both fast and slow fibers, although the proportions of each vary with muscle types. Slow skeletal fibers, often called type I muscles have more structural similarity with cardiac muscle and tend to be used more for fine and postural control. They usually have a greater oxidative capacity and are more resistant to fatigue with continued use. Fast skeletal muscle fibers are divided into fast oxidative (IIa) and fast glycolytic (type IIx/d) fibers. While these muscle fibers have different myosin types, they share many components including the troponin and tropomyosin regulatory proteins. Fast fibers tend to exert greater forces but fatigue faster than slow fibers and are functionally useful for acute, large scale movements such as rising from a chair or correcting falls.

Muscle contraction and force generation is controlled through nervous stimulation by innervating motor neurons. Each motor neuron may innervate many (approximately 100-380) muscle fibers as a contractile whole, termed a motor unit. When a muscle is required to contract, motor neurons send stimuli as nerve impulses (action potentials) from the brain stem or spinal cord to the each fiber within the motor unit. The contact region between nerve and muscle fibers is a specialized synapse called the neuromuscular junction (NMJ). Here, membrane depolarizing action potentials in the nerve are translated into an impulse in the muscle fiber through release of the neurotransmitter acetylcholine (ACh). ACh triggers a second action potential in the muscle that spreads rapidly along the fiber and into invaginations in the membrane, termed t-tubules. T-tubules are physically connected to Ca2+ stores within the sarcoplasmic reticulum (SR) of muscle via the dihydropyridine receptor (DHPR). Stimulation of the DHPR activates a second Ca2+ channel in the SR, the ryanodine receptor, to trigger the release of Ca2+ from stores in the SR to the muscle cytoplasm where it can interact with the troponin complex to initiate muscle contraction. If muscle stimulation stops, calcium is rapidly taken back up into the SR through the ATP dependent Ca2+ pump, SERCA.

Muscle function can become compromised in disease by many mechanisms. Examples include the frailty associated with extreme old age (termed sarcopenia) and muscle wasting that occurs in late stage heart failure and cancer (cachexia). Possibly the most severe form of muscular dysfunction arises from diseases of the motor neurons such as Spinal Muscular Atrophy (SMA) and Amyotrophic Lateral Sclerosis (ALS). Both conditions cause progressive death of motor neurons through causes that are not clear. Surviving motor units attempt to compensate for dying ones by innervating more fibers (termed sprouting) but this can only partially correct muscle function, as muscles are subsequently more prone to problems of coordination and fatigue. Eventually, surviving motor neurons die, resulting in complete paralysis of the affected muscle. Both diseases are commonly fatal through the eventual loss of innervation to the diaphragm, resulting in respiratory failure. SMA is a genetic disorder that arises through the mutation of a protein, SMN1, that appears to be required for the survival and health of motor neurons. The disease is most common in children as the majority of patients only survive until 11-12 years of age. ALS is a disease that arises later in life (Age 50+) and has a rapid progression from initial limb weakness to paralysis and death. Common life expectancy after diagnosis is 3-5 years. The cause of disease for most ALS patients is unknown (termed the spontaneous form) while a small proportion of patients have an inherited form (familial) of disease. Treatment options for both SMA and ALS are limited at this point.

Accordingly, there is a need for the development of new compounds that modulate skeletal muscle. There remains a need for agents that exploit new mechanisms of action and which may have better outcomes in terms of relief of symptoms, safety, and patient mortality, both short-term and long-term and an improved therapeutic index.

Provided is at least one chemical entity chosen from compounds of Formula I:

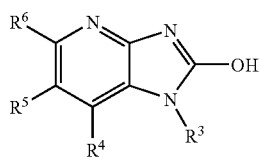

Formula I and pharmaceutically acceptable salts and tautomers thereof, wherein $R^3$ is selected from optionally substituted alkyl, optionally substituted cycloalkyl, optionally substituted aryl, optionally substituted heteroaryl, and optionally substituted heterocycloalkyl;

$R^4$ is selected from optionally substituted aryl and optionally substituted heteroaryl;

$R^5$ is selected from hydrogen, halo, hydroxy, optionally substituted alkyl, optionally substituted alkenyl, optionally substituted amino, optionally substituted alkynyl, optionally substituted cycloalkyl, optionally substituted aryl, optionally substituted heteroaryl, optionally substituted alkoxy, sulfanyl, and sulfinyl; and $R^6$ is selected from hydrogen, halo, hydroxy, lower alkyl, and lower haloalkyl.

Also provided is a pharmaceutically acceptable composition comprising a pharmaceutically acceptable carrier and at least one chemical entity described herein.

Also provided are methods for treating a patient having a condition chosen from neuromuscular disorders, conditions having muscle wasting, claudication, frailty, metabolic syndrome, muscle atrophy associated with disuse, and muscle fatigue, comprising administering to the patient a therapeutically effective amount of at least one chemical entity described herein.

Also provided is a method for treating a patient having a condition chosen from neuromuscular disorders, conditions having muscle wasting, claudication, frailty, metabolic syndrome, muscle atrophy associated with disuse and muscle fatigue comprising administering to the patient a therapeutically effective amount of at least one chemical entity described herein.

Also provided is a method for treating a patient having a condition responsive to modulation of one or more of skeletal myosin, skeletal actin, skeletal tropomyosin, skeletal troponin C, skeletal troponin I, skeletal troponin T, skeletal muscle, and skeletal sarcomere, comprising administering to the patient an effective amount of at least one chemical entity disclosed herein.

Also provided is a method of increasing a function or activity of skeletal muscle, comprising contacting the skeletal muscle with an effective amount of at least one chemical entity disclosed herein.

Also provided is a method of increasing efficiency of skeletal muscle, comprising providing an effective amount of at least one chemical entity disclosed herein and allowing the at least one chemical entity to selectively bind to the troponin complex of fast skeletal muscle fiber of the skeletal muscle, whereby the efficiency of said skeletal muscle is enhanced.

Also provided is a method for increasing time to fast skeletal muscle fiber fatigue, comprising providing an effective amount of at least one chemical entity disclosed herein; allowing the at least one chemical entity to selectively bind to the troponin complex of the fast skeletal muscle fiber of the skeletal muscle; and allowing the fast skeletal muscle fiber to respond with enhanced force and increased time to fatigue as compared to fast skeletal muscle fiber untreated with the chemical entity.

Also provided is a method for sensitizing a fast skeletal muscle fiber to produce force in response to lower concentrations of calcium ion, comprising providing an effective amount of at least one chemical entity disclosed herein; and allowing the at least one chemical entity to selectively bind to the troponin complex of the sarcomere of the fast skeletal muscle fiber and increase the sensitivity of the sarcomere to calcium ion, whereby the fast skeletal muscle fiber produces force in response to lower concentrations of calcium ion.

Also provided is a method for increasing time to skeletal muscle fatigue, comprising providing an effective amount of at least one chemical entity disclosed herein; allowing the at least one chemical entity to selectively bind to the troponin complex of the sarcomere of fast skeletal muscle fiber at a first calcium ion concentration to form a bound complex, whereby the fast skeletal muscle fiber responds with enhanced force and/or increased time to fatigue as compared to fast skeletal muscle fiber exposed to the first calcium ion concentration but not comprising the bound complex.

Other aspects and embodiments will be apparent to those skilled in the art from the following detailed description.

As used in the present specification, the following words and phrases are generally intended to have the meanings as set forth below, except to the extent that the context in which they are used indicates otherwise.

The following abbreviations and terms have the indicated meanings throughout:
Ac=acetyl
ADP=adenosine triphosphate
ATP=adenosine triphosphate
BME=beta-mercaptoethanol
c-=cyclo
CDI=carbonyldiimidazole
DMF=N,N-dimethylformamide
DMSO=dimethyl sulfoxide
(DPPF)PdCl$_2$=[1,1'-bis(diphenylphosphino)ferrocene]dichloropalladium(II)
DTT=Dithiothreitol
EDTA=ethylenediaminetetraacetic acid
Et=ethyl
EtOAc=ethyl acetate
EtOH=ethanol
g=gram
h or hr=hour
i-=iso
kg or Kg=kilogram
l or L=liter
LCMS=liquid chromatography-mass spectrometry
m/z=mass-to-charge ratio
Me=methyl
NMR=nuclear magnetic resonance
min=minute
mg=milligram
min=minute
mL or ml=milliliter
mmol=millimole
MMP=matrixmetalloproteinase
MW=microwave
n-=normal
Ph=phenyl
(Ph$_3$P)$_4$Pd=tetrakis(triphenylphosphine)palladium(0)
(Ph$_3$P)$_2$PdCl$_2$=dichlorobis(triphenylphosphine)palladium(II)
rpm=revolutions per minute
rt or RT=room temperature
s-=sec-=secondary
t-=tert-=tertiary
THF=tetrahydrofuran
vol=volume equivalent in mL/g or L/Kg for the limiting reagent unless otherwise indicated By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible, and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to seven carbons. In certain embodiments, "lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

"Alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

"Alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons.

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2H$, —C(O)$OC_1$-$C_4$ alkyl, CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

In some embodiments, a substituted alkoxy group is "polyalkoxy" or —O— (optionally substituted alkylene)-(optionally substituted alkoxy), and includes groups such as —$OCH_2CH_2OCH_3$, and residues of glycol ethers such as polyethyleneglycol, and —O($CH_2CH_2O)_xCH_3$, where x is an integer of 2-20, such as 2-10, and for example, 2-5. Another substituted alkoxy group is hydroxyalkoxy or —$OCH_2(CH_2)_y$OH, where y is an integer of 1-10, such as 1-4.

The term "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —OP(O)($OR^b$)$OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2H$, —C(O)$OC_1$-$C_4$ alkyl, CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

"Acyl" refers to the groups H—C(O)—, (alkyl)-C(O)—, (aryl)-C(O)—, (heteroaryl)-C(O)—, and (heterocycloalkyl)-C(O)—, wherein the group is attached to the parent structure through the carbonyl functionality, and wherein alkyl, aryl, heteroaryl, and heterocycloalkyl are optionally substituted as described herein. Examples include acetyl, benzoyl, propionyl, isobutyryl, t-butoxycarbonyl, benzyloxycarbonyl and the like. "Lower-acyl" refers to groups containing one to six carbons and "acyloxy" refers to the group O-acyl.

The term "amino" refers to the group —$NH_2$.

The term "substituted amino" refers to the group —$NHR^d$ or —$NR^dR^e$ wherein $R^d$ is chosen from hydroxy, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and $R^e$ is chosen from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as $CO_2R^b$), aminocarbonyl (such as —$CONR^bR^c$), —$OCOR^b$, —$OCO_2R^a$, —$OCONR^bR^c$, —$OCONR^bR^c$, —OP(O)($OR^b$)$OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "aminocarbonyl" refers to the group —$CONR^b R^c$, where $R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"Halogen" or "halo" refers to fluorine, chlorine, bromine or iodine. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroaryl" encompasses:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O⁻) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. Compounds described herein are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Compounds of Formula I are tautomeric.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

The term "pharmaceutically acceptable salt" refers to salts that retain the biological effectiveness and properties of the compounds described herein and, which are not biologically or otherwise undesirable. In many cases, the compounds described herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemihydrates.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "sulfanyl" refers to the groups: —S-(optionally substituted alkyl), —S-(optionally substituted cycloalkyl), —S-(optionally substituted aryl), —S-(optionally substituted heteroaryl), and —S-(optionally substituted heterocycloalkyl).

The term "sulfinyl" refers to the groups: —S(O)—H, —S(O)-(optionally substituted alkyl), —S(O)-(optionally substituted cycloalkyl), —S(O)-(optionally substituted amino), —S(O)-(optionally substituted aryl), —S(O)-(optionally substituted heteroaryl), and —S(O)-(optionally substituted heterocycloalkyl).

The term "sulfonyl" refers to the groups: —$S(O_2)$—H, —$S(O_2)$—(optionally substituted alkyl), —$S(O_2)$—(optionally substituted cycloalkyl), —$S(O_2)$—(optionally substituted amino), —$S(O_2)$—(optionally substituted aryl), —$S(O_2)$—(optionally substituted heteroaryl), and —$S(O_2)$—(optionally substituted heterocycloalkyl).

As used herein, the term "therapeutic" refers to a compound that is believed to be capable of modulating the contractility of the skeletal sarcomere, skeletal muscle fiber, or skeletal muscle in vivo that can have application in both human or animal disease. Modulation would be desirable in a number of conditions or diseases, including, but not limited to, neuromuscular disorders (e.g., ALS), conditions having muscle wasting (e.g., sarcopenia and cachexia syndromes), claudication, frailty, metabolic syndrome, muscle atrophy associated with disuse, muscle spasms, obesity, and other acute and chronic conditions and diseases.

The term "therapeutically effective amount" or "effective amount" refers to that amount of a compound selected from Formula I that is sufficient to effect treatment, as defined below, when administered to a mammal in need of such treatment, e.g., a therapeutically effective amount may be an amount sufficient to treat a disease responsive to activation of skeletal muscle. The therapeutically effective amount will vary depending upon the subject and disease condition being treated, the weight and age of the subject, the severity of the disease condition, the particular compound selected from Formula I, the dosing regimen to be followed, timing of administration, the manner of administration and the like, all of which can readily be determined by one of ordinary skill in the art. The therapeutically effective amount may be ascertained experimentally, for example by assaying blood concentration of the chemical entity, or theoretically, by calculating bioavailability.

"ATPase" refers to an enzyme that hydrolyzes ATP. ATPases include proteins comprising molecular motors such as the myosins.

As used herein, "frailty" is a syndrome characterized by meeting at least one of the following five attributes: unintentional weight loss, muscle weakness, slow walking speed, exhaustion, and low physical activity.

As used herein, "cachexia" means a state often associated with cancer or other serious diseases or conditions, (e.g., chronic obstructive pulmonary disease, chronic kidney disease), that is characterized by progressive weight loss, muscle atrophy and fatigue, due to the deletion of adipose tissue and skeletal muscle.

As used herein, "muscle spasm" means an involuntary contraction of a muscle. Muscle spasms may lead to cramps.

As used herein, "post-surgical muscle weakness" refers to a reduction in the strength of one or more muscles following surgical procedure. Weakness may be generalized (i.e. total body weakness) or localized to a specific area, side of the body, limb, or muscle.

As used herein, "post-traumatic muscle weakness" refers to a reduction in the strength of one or more muscles following a traumatic episode (e.g. bodily injury). Weakness may be generalized (i.e. total body weakness) or localized to a specific area, side of the body, limb, or muscle.

As used herein, "neuromuscular disease" means any disease that affects any part of the nerve and muscle. Neuromuscular disease encompasses critical illness polyneuropathy, prolonged neuromuscular blockade, acute myopathy as well as acute inflammatory demyelinating polyradiculoneuropathy, amyotrophic lateral sclerosis (ALS), autonomic neuropathy, Charcot-Marie-Tooth disease and other hereditary motor and sensory neuropathies, chronic inflammatory demyelinating polyradiculoneuropathy, dermatomyositis/polymyositis, diabetic neuropathy, dystrophinopathies, endocrine myopathies, focal muscular atrophies, hemifacial spasm, hereditary neuropathies of the Charcot-Marie-Tooth disease type, inclusion body myositis, Kennedy disease, Lambert-Eaton myasthenic syndrome, muscular dystrophy (e.g., limb-girdle, Duchenne, Becker, myotonic, facioscapulohumeral, etc.), metabolic myopathies, metabolic neuropathy, multifocal motor neuropathy with conduction blocks, myasthenia gravis, neuropathy of Friedreich Ataxia, neuropathy of leprosy, nutritional neuropathy, periodic paralyses, primary lateral sclerosis, restrictive lung disease, sarcoidosis and neuropathy, Schwartz-Jampel Syndrome, spinal muscle atrophy, stiff person syndrome, thyroid disease, traumatic peripheral nerve lesions, vasculitic neuropathy, among others.

As used herein "obesity" means having a body mass index (BMI) greater than or equal to 30 kg/m$^2$. BMI is defined as weight (kg) divided by height (m$^2$). Obesity encompasses hyperplastic obesity, an increase in the number of fat cells, and hypertrophic obesity, an increase in the size of the fat cells. Overweight is defined as having a BMI from 25 up to 30 kg/m$^2$; obesity as a BMI greater than or equal to 30 kg/m$^2$, as stated above, and severe (or morbid) obesity is defined as a BMI greater than or quality to 40 kg/m$^2$.

As used herein, "sarcopenia" means a loss of skeletal muscle mass, quality, and strength. Often sarcopenia is associated with ageing, but is also associated with HIV infection. Sarcopenia may lead to frailty, for example, in the elderly.

As used herein, "wasting syndrome" means a condition characterized by involuntary weight loss associated with chronic fever and diarrhea. In some instances, patients with wasting syndrome lose 10% of baseline body weight within one month.

Compounds of Formula I also include crystalline and amorphous forms of those compounds, including, for example, polymorphs, pseudopolymorphs, solvates (including hydrates), unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates (including hydrates), unsolvated polymorphs (including anhydrates), conformational polymorphs, and amorphous forms, as well as mixtures thereof, unless a particular crystalline or amorphous form is referred to. Compounds of Formula I also include pharmaceutically acceptable forms of the recited compounds, including chelates, non-covalent complexes, prodrugs, and mixtures thereof.

Chemical entities include, but are not limited to, compounds of Formula I and all pharmaceutically acceptable salts thereof. Hence, the terms "chemical entity" and "chemical entities" also encompass pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n ranges from 0 to 4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of compounds of Formula I, for example, ester or amide derivatives of the compounds of Formula I. The term "prodrug" includes any compound that becomes a compound of Formula I when administered to a patient, e.g., upon metabolic processing of the prodrug. Examples of prodrugs include, but are not limited to, acetate, formate, benzoate, and like derivatives of functional groups (such as alcohol or amine groups) in the compounds of Formula I.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "active agent" is used to indicate a chemical entity which has biological activity. In certain embodiments, an "active agent" is a compound having therapeutic utility. In some embodiments, the chemical entity enhances at least one aspect of skeletal muscle function or activity, such as power output, skeletal muscle force, skeletal muscle endurance, oxygen consumption, efficiency, calcium sensitivity, and the like.

As used herein, "skeletal muscle" includes skeletal muscle tissue as well as components thereof, such as skeletal muscle fibers (i.e., fast or slow skeletal muscle fibers), the myofibrils comprising the skeletal muscle fibers, the skeletal sarcomere which comprises the myofibrils, and the various components of the skeletal sarcomere described above. Skeletal muscle does not include cardiac muscle or a combination of sarcomeric components that occurs in its entirety in cardiac muscle.

As used herein, "efficiency" or "muscle efficiency" means the ratio of mechanical work output to the total metabolic cost.

As used herein, "power output" of a muscle means work/cycle time and may be scaled up from PoLo/cycle time units based on the properties of the muscle. Power output may be modulated by changing, for example, activating parameters during cyclical length changes, including timing of activation (phase of activation) and the period of activation (duty cycle.)

By "significant" is meant any detectable change that is statistically significant in a standard parametric test of statistical significance, e.g., Student's T-test, where p<0.05.

"Patient" refers to an animal, such as a mammal, for example, a human, that has been or will be the object of treatment, observation or experiment. The methods described herein can be useful in both human therapy and veterinary applications. In some embodiments, the patient is a mammal, and in some embodiments, the patient is human.

"Treatment" or "treating" means any treatment of a disease in a patient, including:
 (a) preventing the disease, that is, causing the clinical symptoms of the disease not to develop;
 (b) inhibiting the disease;
 (c) slowing or arresting the development of clinical symptoms; and/or
 (d) relieving the disease, that is, causing the regression of clinical symptoms.

As used herein, "modulation" refers to a change in function or efficiency in one or more of skeletal myosin, skeletal actin, skeletal tropomyosin, the skeletal troponin complex of the skeletal sarcomere, skeletal troponin C, skeletal troponin I, skeletal troponin T, and skeletal muscle, including fragments and isoforms thereof, as well as the skeletal sarcomere as a direct or indirect response to the presence of at least one chemical entity described herein, relative to the activity of the myosin or sarcomere in the absence of the compound. The change may be an increase in activity (potentiation) or a decrease in activity (inhibition), and may be due to the direct interaction of the compound with myosin or the sarcomere, or due to the interaction of the compound with one or more other factors that in turn effect one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere, for example, through sensitization of the skeletal myosin or the sarcomere to contraction at lower Ca2+ concentrations.

As used herein, "selective binding" or "selectively binding" refers to preferential binding to a target protein in one type of muscle or muscle fiber as opposed to other types. For example, a compound selective binds if that compound preferentially binds troponin C in the troponin complex of a fast skeletal muscle fiber or sarcomere in comparison with troponin C in the troponin complex of a slow muscle fiber or sarcomere or with troponin C in the troponin complex of a cardiac sarcomere.

Provided is at least one chemical entity chosen from compounds of Formula I:

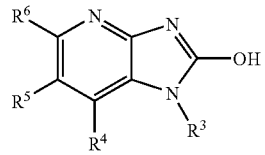

Formula I and pharmaceutically acceptable salts and tautomers thereof, wherein
$R^3$ is selected from optionally substituted alkyl, optionally substituted cycloalkyl, optionally substituted aryl, optionally substituted heteroaryl, and optionally substituted heterocycloalkyl;
$R^4$ is selected from optionally substituted aryl and optionally substituted heteroaryl;
$R^5$ is selected from hydrogen, halo, hydroxy, optionally substituted alkyl, optionally substituted amino, optionally substituted alkenyl, optionally substituted alkynyl, optionally substituted cycloalkyl, optionally substituted aryl, optionally substituted heteroaryl, optionally substituted alkoxy, sulfanyl, and sulfinyl; and
$R^6$ is selected from hydrogen, halo, hydroxy, lower alkyl, and lower haloalkyl.

In some embodiments, $R^3$ is selected from optionally substituted heterocycloalkyl, optionally substituted cycloalkyl, and optionally substituted lower alkyl. In some embodiments, $R^3$ is lower alkyl optionally substituted with one or more groups chosen from optionally substituted phenyl, hydroxy, optionally substituted alkoxy, optionally substituted amino, optionally substituted heteroaryl, halo, and optionally substituted heterocycloalkyl. In some embodiments, $R^3$ is selected from alkenyl, pentyl, cyclopropyl, butyl, propyl, ethyl, and methyl, each of which is optionally substituted with one or more groups chosen from optionally substituted phenyl, hydroxy, optionally substituted alkoxy, optionally substituted amino, and optionally substituted heterocycloalkyl. In some embodiments, $R^3$ is selected from 3-pentyl, isopropyl, tert-butyl, 1-ethyl-2-hydroxyethyl, 1-methyl-2-hydroxyethyl, 1-ethyl-3-hydroxypropyl, 1-hydroxymethylpropyl, 3-hydroxypropyl, 2-hydroxyethyl, isopropyl, 1-hydroxymethyl-3-methylbutyl, 1-(methoxymethyl)propyl, 1-ethyl-2-hydroxy-2-methylpropyl, 2-hydroxy-tert-butyl, 1-ethyl-2-hydroxy-2-methylpropyl, and 2-hydroxy-1-(2-methylpropyl)ethyl. In some embodiments, $R^3$ is selected from 3-pentyl, isopropyl, 1-ethyl-2-hydroxyethyl, 1-methyl-2-hydroxethyl, tert-butyl, 1-ethyl-3-hydroxypropyl, 1-hydroxymethyl-3-methylbutyl, 1-(methoxymethyl)propyl, 1-ethyl-2-hydroxy-2-methylpropyl, and 2-hydroxy-tert-buyl. In some embodiments, $R^3$ is selected from (S)-1-hydroxy-4-methylpentan-2-yl; (S)-1-hydroxy-butan-2-yl; 1-acetoxybutan-2-yl; (R)-1-methoxybut-2-yl; (S)-1-methoxybut-2-yl; (S)-1-hydroxy-pentan-3-yl; (R)-2-hydroxy-2-methylpentan-3-yl; (S)-2-hydroxy-2-methylpentan-3-yl; (S)-1-hydroxy-pentan-2-yl; (S)-1-hydroxy-butan-2-yl; (R)-1-hydroxy-propan-2-yl; (S)-1-hydroxy-propan-2-yl; (S)-4-hydroxy-butan-2-yl; (R)-1-hydroxy-butan-2-yl; (S)—((S)-2-butyl)-2-amino-3-methylbutanoate; (S)-1-aminobutan-2-yl; and (R)—((S)-2-butyl)-2-amino-3-methylbutanoate. In some embodiments, $R^3$ is selected from 3-pentyl, isopropyl, (S)-1-hydroxy-pentan-3-yl, and (S)-1-hydroxy-butan-2-yl. In some embodiments, $R^3$ is selected from 3-pentyl. In some embodiments, $R^3$ is methylpropyl. In some embodiments, $R^3$ is (1R)-1-methylpropyl.

In some embodiments, $R^4$ is selected from optionally substituted phenyl, optionally substituted oxadiazolyl, optionally substituted pyrazolyl, optionally substituted indazolyl, optionally substituted benzimidazolyl, optionally substituted tetrazolyl, and optionally substituted pyridyl. In some embodiments, $R^4$ is selected from optionally substituted phenyl, optionally substituted pyrid-2-yl and optionally substituted pyrid-4-yl. In some embodiments, $R^4$ is selected from phenyl, pyrid-2-yl and pyrid-4-yl, each of which is optionally substituted with one or two groups independently chosen from optionally substituted lower alkyl, halo, cyano, sulfonyl, optionally substituted lower alkoxy, aminocarbonyl, optionally substituted amino, alkoxycarbonyl, and acyl. In some embodiments, $R^4$ is optionally substituted pyrazolyl. In some embodiments, $R^4$ is pyrazol-1-yl or pyrazol-3-yl, each of which is optionally substituted with one or two groups independently chosen from lower alkyl, halo, and lower alkoxy. In some embodiments, $R^4$ is pyrazol-1-yl.

In some embodiments, $R^5$ is selected from hydrogen, halo, optionally substituted alkynyl, optionally substituted alkenyl, optionally substituted alkyl, optionally substituted amino, optionally substituted alkoxy, and sulfanyl. In some embodiments, $R^5$ is selected from hydrogen, halo, and optionally substituted alkynyl. In some embodiments, $R^5$ is selected from hydrogen, fluoro, chloro, and bromo. In some embodiments, $R^5$ is chloro.

In some embodiments, $R^6$ is selected from hydrogen, halo, and lower alkyl. In some embodiments, $R^6$ is hydrogen.

Also provided is at least one chemical entity chosen from compounds of Formula II:

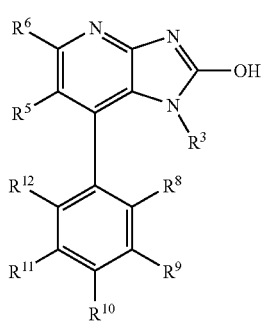

Formula II and pharmaceutically acceptable salts thereof, wherein $R^3$, $R^5$, and $R^6$ are as described for compounds of Formula I and wherein $R^8$ and $R^{12}$ are independently selected from hydrogen, halo, optionally substituted lower alkyl, cyano, and acyl;

$R^9$ and $R^{11}$ are independently selected from hydrogen, halo, acyl, lower alkoxy, cyano, lower alkoxy carbonyl, and optionally substituted lower alkyl; and $R^{10}$ is selected from hydrogen, halo, hydroxy, cyano, optionally substituted lower alkyl, sulfonyl, aminocarbonyl, and optionally substituted lower alkoxy.

In some embodiments, $R^8$ is selected from hydrogen, halo, optionally substituted methyl, optionally substituted alkoxy and cyano. In some embodiments, $R^8$ is selected from hydrogen, fluoro, chloro, trifluoromethyl, methoxy, methyl, and cyano. In some embodiments, $R^8$ is selected from hydrogen and fluoro. In some embodiments, $R^8$ is hydrogen.

In some embodiments, $R^9$ is selected from hydrogen, lower alkyl, and halo. In some embodiments, $R^9$ is selected from fluoro, chloro, methyl, and hydrogen. In some embodiments, $R^9$ is selected from fluoro and hydrogen.

In some embodiments, $R^{10}$ is selected from hydrogen, halo, optionally substituted methoxy, optionally substituted methyl, and cyano. In some embodiments, $R^{10}$ is selected from hydrogen, halo, methoxy, trifluoromethoxy, trifluoromethyl, methyl, and cyano. In some embodiments, $R^{10}$ is selected from hydrogen, chloro, and fluoro.

In some embodiments, $R^{11}$ is hydrogen.
In some embodiments, $R^{12}$ is hydrogen.
In some embodiments, the compound of Formula I is chosen from
7-(2H-1,2,3,4-tetraazol-5-yl)-6-chloro-1-(ethylpropyl)imidazo[4,5-b]pyridin-2-ol
6-chloro-1-(ethylpropyl)-7-(2-methyl(1,2,3,4-tetraazol-5-yl))imidazo[4,5-b]pyridin-2-ol
6-chloro-1-(ethylpropyl)-2-methoxy-7-(2-methyl(1,2,3,4-tetraazol-5-yl))imidazo[4,5-b]pyridine
6-chloro-1-(ethylpropyl)-7-(5-methyl(1,2,4-oxadiazol-3-yl))imidazo[4,5-b]pyridin-2-ol
6-chloro-1-(ethylpropyl)-7-phenylimidazo[4,5-b]pyridin-2-ol
6-chloro-1-(ethylpropyl)-7-(1-methylpyrazol-4-yl)imidazo[4,5-b]pyridin-2-ol
6-chloro-1-(ethylpropyl)-7-(4-pyridyl)imidazo[4,5-b]pyridin-2-ol
6-chloro-1-(ethylpropyl)-7-(4-fluorophenyl)imidazo[4,5-b]pyridin-2-ol
6-chloro-7-(4-chlorophenyl)-1-(ethylpropyl)imidazo[4,5-b]pyridin-2-ol
6-chloro-1-(ethylpropyl)-7-(3-pyridyl)imidazo[4,5-b]pyridin-2-ol
6-chloro-1-(ethylpropyl)-7-(3-fluorophenyl)imidazo[4,5-b]pyridin-2-ol
1-(ethylpropyl)-7-phenylimidazo[4,5-b]pyridin-2-ol
6-chloro-1-(ethylpropyl)-7-pyrimidin-5-ylimidazo[4,5-b]pyridin-2-ol
6-chloro-7-(3-chlorophenyl)-1-(ethylpropyl)imidazo[4,5-b]pyridin-2-ol
4-[6-chloro-1-(ethylpropyl)-2-hydroxyimidazo[4,5-b]pyridin-7-yl]benzenecarbonitrile
3-[6-chloro-1-(ethylpropyl)-2-hydroxyimidazo[4,5-b]pyridin-7-yl]benzenecarbonitrile
6-chloro-1-(ethylpropyl)-7-(4-methylphenyl)imidazo[4,5-b]pyridin-2-ol
1-[6-chloro-1-(ethylpropyl)-2-hydroxyimidazo[4,5-b]pyridin-7-yl]-4-(methylsulfonyl)benzene
4-[6-chloro-1-(ethylpropyl)-2-hydroxyimidazo[4,5-b]pyridin-7-yl]benzamide
6-chloro-1-(ethylpropyl)-7-[3-(hydroxymethyl)phenyl]imidazo[4,5-b]pyridin-2-ol
6-chloro-1-(ethylpropyl)-7-[4-(methoxymethyl)phenyl]imidazo[4,5-b]pyridin-2-ol
6-chloro-1-(ethylpropyl)-7-(4-methoxyphenyl)imidazo[4,5-b]pyridin-2-ol
1-[6-chloro-1-(ethylpropyl)-2-hydroxyimidazo[4,5-b]pyridin-7-yl]-3-(methylsulfonyl)benzene
6-chloro-1-(ethylpropyl)-7-(4-hydroxyphenyl)imidazo[4,5-b]pyridin-2-ol
6-chloro-1-(ethylpropyl)-7-[4-(trifluoromethoxy)phenyl]imidazo[4,5-b]pyridin-2-ol
{3-[6-chloro-1-(ethylpropyl)-2-hydroxyimidazo[4,5-b]pyridin-7-yl]phenyl}-N,N-dimethylcarboxamide
6-chloro-1-(ethylpropyl)-7-(3-methoxyphenyl)imidazo[4,5-b]pyridin-2-ol
3-[6-chloro-1-(ethylpropyl)-2-hydroxyimidazo[4,5-b]pyridin-7-yl]benzamide
6-chloro-1-(ethylpropyl)-7-[3-(methoxymethyl)phenyl]imidazo[4,5-b]pyridin-2-ol
{4-[6-chloro-1-(ethylpropyl)-2-hydroxyimidazo[4,5-b]pyridin-7-yl]phenyl}-N,N-dimethylcarboxamide
6-chloro-1-(ethylpropyl)-7-(2-methylphenyl)imidazo[4,5-b]pyridin-2-ol
6-chloro-1-(ethylpropyl)-7-indol-4-ylimidazo[4,5-b]pyridin-2-ol
6-chloro-1-(ethylpropyl)-7-(2-fluorophenyl)imidazo[4,5-b]pyridin-2-ol
6-chloro-1-(ethylpropyl)-7-(6-methoxy(3-pyridyl))imidazo[4,5-b]pyridin-2-ol
6-chloro-1-(ethylpropyl)-7-[3-(trifluoromethoxy)phenyl]imidazo[4,5-b]pyridin-2-ol 6-chloro-1-(ethylpropyl)-7-(3-hydroxyphenyl)imidazo[4,5-b]pyridin-2-ol
N-{4-[6-chloro-1-(ethylpropyl)-2-hydroxyimidazo[4,5-b]pyridin-7-yl]phenyl}acetamide
6-chloro-1-(ethylpropyl)-7-pyrazol-3-ylimidazo[4,5-b]pyridin-2-ol
6-chloro-1-(ethylpropyl)-7-pyrazol-4-ylimidazo[4,5-b]pyridin-2-ol
7-(3,4-difluorophenyl)-6-chloro-1-(ethylpropyl)imidazo[4,5-b]pyridin-2-ol
6-chloro-1-(ethylpropyl)-7-(2-pyridyl)imidazo[4,5-b]pyridin-2-ol
6-chloro-1-(ethylpropyl)-7-(3-methylphenyl)imidazo[4,5-b]pyridin-2-ol
6-chloro-1-(ethylpropyl)-7-[4-(trifluoromethyl)phenyl]imidazo[4,5-b]pyridin-2-ol
7-[4-(aminomethyl)phenyl]-6-chloro-1-(ethylpropyl)imidazo[4,5-b]pyridin-2-ol
6-chloro-1-(ethylpropyl)-7-(2-methoxy(4-pyridyl))imidazo[4,5-b]pyridin-2-ol
6-chloro-1-(ethylpropyl)-7-(5-methoxy(3-pyridyl))imidazo[4,5-b]pyridin-2-ol
6-chloro-7-(4-chloro-3-fluorophenyl)-1-(ethylpropyl)imidazo[4,5-b]pyridin-2-ol
6-chloro-1-(ethylpropyl)-7-(4-morpholin-4-ylphenyl)imidazo[4,5-b]pyridin-2-ol
{4-[6-chloro-1-(ethylpropyl)-2-hydroxyimidazo[4,5-b]pyridin-7-yl]phenyl}(methylsulfonyl)amine
6-chloro-1-(ethylpropyl)-7-[4-(hydroxymethyl)phenyl]imidazo[4,5-b]pyridin-2-ol methyl 3-[6-chloro-1-(ethylpropyl)-2-hydroxyimidazo[4,5-b]pyridin-7-yl]benzoate
3-[6-chloro-1-(ethylpropyl)-2-hydroxyimidazo[4,5-b]pyridin-7-yl]benzoic acid
6-chloro-1-(ethylpropyl)-7-[4-(1-hydroxy-isopropyl)phenyl]imidazo[4,5-b]pyridin-2-ol
2-[6-chloro-1-(ethylpropyl)-2-hydroxyimidazo[4,5-b]pyridin-7-yl]benzoic acid
6-chloro-1-(ethylpropyl)-7-[3-(1-hydroxy-isopropyl)phenyl]imidazo[4,5-b]pyridin-2-ol
1-((1S)-1-ethyl-2-hydroxyethyl)-6-chloro-7-(4-chlorophenyl)imidazo[4,5-b]pyridin-2-ol
1-((1R and 1S)-1-ethyl-2-hydroxyethyl)-6-chloro-7-(4-chlorophenyl)imidazo[4,5-b]pyridin-2-ol
4-(6-chloro-2-hydroxy-1-(pentan-3-yl)-1H-imidazo[4,5-b]pyridin-7-yl)-2-fluorobenzonitrile
6-chloro-1-(ethylpropyl)-7-(2-methyl(4-pyridyl))imidazo[4,5-b]pyridin-2-ol
4-(6-chloro-2-hydroxy-1-(pentan-3-yl)-1H-imidazo[4,5-b]pyridin-7-yl)picolinonitrile
7-[3-(aminomethyl)phenyl]-6-chloro-1-(ethylpropyl)imidazo[4,5-b]pyridin-2-ol
6-chloro-1-(ethylpropyl)-7-[2-(methoxymethyl)phenyl]imidazo[4,5-b]pyridin-2-ol
6-chloro-1-(ethylpropyl)-7-(6-methoxy(2-pyridyl))imidazo[4,5-b]pyridin-2-ol
7-(1H-indazol-5-yl)-6-chloro-1-(ethylpropyl)imidazo[4,5-b]pyridin-2-ol
7-(1H-indazol-6-yl)-6-chloro-1-(ethylpropyl)imidazo[4,5-b]pyridin-2-ol
6-chloro-1-(ethylpropyl)-7-(5-hydroxy(3-pyridyl))imidazo[4,5-b]pyridin-2-ol
6-chloro-1-(ethylpropyl)-7-(3-fluoro-4-methoxyphenyl)imidazo[4,5-b]pyridin-2-ol
N-({4-[6-chloro-1-(ethylpropyl)-2-hydroxyimidazo[4,5-b]pyridin-7-yl]phenyl}methyl)acetamide
7-{4-[(dimethylamino)methyl]phenyl}-6-chloro-1-(ethylpropyl)imidazo[4,5-b]pyridin-2-ol
(tert-butoxy)-N-{4-[6-chloro-1-(ethylpropyl)-2-hydroxyimidazo[4,5-b]pyridin-7-yl]phenyl}-N-methylcarboxamide
6-chloro-1-(ethylpropyl)-7-(2-fluoro-4-methoxyphenyl)imidazo[4,5-b]pyridin-2-ol
4-[6-chloro-1-(ethylpropyl)-2-hydroxyimidazo[4,5-b]pyridin-7-yl]benzoic acid
1-((1R and 1S)-1-ethyl-2-hydroxyethyl)-6-chloro-7-(4-fluorophenyl)imidazo[4,5-b]pyridin-2-ol
6-chloro-1-(ethylpropyl)-7-[4-(hydroxyethyl)phenyl]imidazo[4,5-b]pyridin-2-ol
6-chloro-7-(4-fluorophenyl)-1-methylimidazo[4,5-b]pyridin-2-ol
6-chloro-7-(4-fluorophenyl)-1-prop-2-enylimidazo[4,5-b]pyridin-2-ol
6-chloro-7-(4-fluorophenyl)-1-(methylethyl)imidazo[4,5-b]pyridin-2-ol
2-[6-chloro-1-(ethylpropyl)-2-hydroxyimidazo[4,5-b]pyridin-7-yl]benzenecarbonitrile
7-{3-[(dimethylamino)methyl]phenyl}-6-chloro-1-(ethylpropyl)imidazo[4,5-b]pyridin-2-ol
7-{2-[(dimethylamino)methyl]phenyl}-6-chloro-1-(ethylpropyl)imidazo[4,5-b]pyridin-2-ol
2-[6-chloro-1-(ethylpropyl)-2-hydroxyimidazo[4,5-b]pyridin-7-yl]benzaldehyde
3-[6-chloro-1-(ethylpropyl)-2-hydroxyimidazo[4,5-b]pyridin-7-yl]benzaldehyde
N-({3-[6-chloro-1-(ethylpropyl)-2-hydroxyimidazo[4,5-b]pyridin-7-yl]phenyl}methyl)acetamide
2-[6-chloro-1-(ethylpropyl)-2-hydroxyimidazo[4,5-b]pyridin-7-yl]benzamide
6-chloro-7-(2-chloro-4-methylphenyl)-1-(ethylpropyl)imidazo[4,5-b]pyridin-2-ol
6-chloro-7-(2-chloro-4-methoxyphenyl)-1-(ethylpropyl)imidazo[4,5-b]pyridin-2-ol
1-((1S)-2-hydroxy-isopropyl)-6-chloro-7-(4-chlorophenyl)imidazo[4,5-b]pyridin-2-ol
1-((1S)-2-hydroxy-isopropyl)-6-chloro-7-(4-fluorophenyl)imidazo[4,5-b]pyridin-2-ol
6-chloro-1-(ethylpropyl)-7-(5-methylpyrimidin-2-yl)imidazo[4,5-b]pyridin-2-ol
1-((1S)-1-ethyl-2-hydroxyethyl)-6-chloro-7-phenylimidazo[4,5-b]pyridin-2-ol
1-((1R)-2-hydroxy-isopropyl)-6-chloro-7-(4-fluorophenyl)imidazo[4,5-b]pyridin-2-ol
6-chloro-1-(ethylpropyl)-7-(1-methyl(1H-indazol-5-yl))imidazo[4,5-b]pyridin-2-ol
6-chloro-1-(ethylpropyl)-7-(1-methyl(1H-indazol-6-yl))imidazo[4,5-b]pyridin-2-ol
6-chloro-7-(5-chloro(3-pyridyl))-1-(ethylpropyl)imidazo[4,5-b]pyridin-2-ol
2-[6-chloro-7-(4-fluorophenyl)-2-hydroxyimidazo[4,5-b]pyridinyl]propane-1,3-diol
1-(tert-butyl)-6-chloro-7-(4-fluorophenyl)imidazo[4,5-b]pyridin-2-ol
6-chloro-1-(ethylpropyl)-7-(6-methyl(2-pyridyl))imidazo[4,5-b]pyridin-2-ol
6-chloro-1-(ethylpropyl)-7-(4-methyl(2-pyridyl))imidazo[4,5-b]pyridin-2-ol
6-chloro-1-(ethylpropyl)-7-(5-methyl(2-pyridyl))imidazo[4,5-b]pyridin-2-ol
6-chloro-1-(ethylpropyl)-7-(6-methyl(3-pyridyl))imidazo[4,5-b]pyridin-2-ol
6-chloro-1-(ethylpropyl)-7-[2-(trifluoromethyl)(4-pyridyl)]imidazo[4,5-b]pyridin-2-ol
6-chloro-1-(1-ethyl-2-hydroxyethyl)-7-(2-pyridyl)imidazo[4,5-b]pyridin-2-ol 6-chloro-1-(2-hydroxyethyl)-7-phenylimidazo[4,5-b]pyridin-2-ol
1-((1R)-1-ethyl-3-hydroxypropyl)-6-chloro-7-(4-fluorophenyl)imidazo[4,5-b]pyridin-2-ol
1-((1S)-1-ethyl-3-hydroxypropyl)-6-chloro-7-(4-fluorophenyl)imidazo[4,5-b]pyridin-2-ol
6-chloro-7-(3-chloro(4-pyridyl))-1-(ethylpropyl)imidazo[4,5-b]pyridin-2-ol
1-((1S)-1-ethyl-2-hydroxyethyl)-7-(3,4-difluorophenyl)-6-chloroimidazo[4,5-b]pyridin-2-ol
6-chloro-1-(ethylpropyl)-7-(5-fluoro(3-pyridyl))imidazo[4,5-b]pyridin-2-ol
6-chloro-7-(4-fluorophenyl)-1-(3-hydroxypropyl)imidazo[4,5-b]pyridin-2-ol
1-((1S)-3-hydroxy-1-methylpropyl)-6-chloro-7-(4-fluorophenyl)imidazo[4,5-b]pyridin-2-ol
(2S)-2-[7-(3,4-difluorophenyl)-6-chloro-2-hydroxyimidazo[4,5-b]pyridinyl]butyl (2S)-2-amino-3-methylbutanoate
1-((1S)-1-ethyl-2-hydroxyethyl)-6-chloro-7-(4-methoxyphenyl)imidazo[4,5-b]pyridin-2-ol
6-chloro-1-(ethylpropyl)-7-(5-fluoro(2-pyridyl))imidazo[4,5-b]pyridin-2-ol
6-chloro-1-(ethylpropyl)-7-(3-fluoro(4-pyridyl))imidazo[4,5-b]pyridin-2-ol
1-((1S)-1-ethyl-2-hydroxyethyl)-6-chloro-7-(4-methylphenyl)imidazo[4,5-b]pyridin-2-ol
4-[1-((1S)-1-ethyl-2-hydroxyethyl)-6-chloro-2-hydroxyimidazo[4,5-b]pyridin-7-yl]benzenecarbonitrile
6-chloro-7-(5-chloro(2-pyridyl))-1-(methylethyl)imidazo[4,5-b]pyridin-2-ol
6-chloro-7-(5-chloro(2-pyridyl))-1-(ethylpropyl)imidazo[4,5-b]pyridin-2-ol
1-((1S)-1-ethyl-2-hydroxyethyl)-6-chloro-7-(5-chloro(2-pyridyl))imidazo[4,5-b]pyridin-2-ol
6-chloro-7-(5-fluoro(2-pyridyl))-1-(methylethyl)imidazo[4,5-b]pyridin-2-ol
2-[7-(3,4-difluorophenyl)-6-chloro-2-hydroxyimidazo[4,5-b]pyridinyl]butyl dihydrogen phosphate
(2S)-2-[6-chloro-7-(4-fluorophenyl)-2-hydroxyimidazo[4,5-b]pyridinyl]butyl dihydrogen phosphate
(2S)-2-[6-chloro-7-(4-fluorophenyl)-2-hydroxyimidazo[4,5-b]pyridinyl]butyl (2S)-2-amino-3-methylbutanoate
6-[6-chloro-1-(ethylpropyl)-2-hydroxyimidazo[4,5-b]pyridin-7-yl]pyridine-3-carbonitrile
6-[1-((1S)-1-ethyl-2-hydroxyethyl)-6-chloro-2-hydroxyimidazo[4,5-b]pyridin-7-yl]pyridine-3-carbonitrile
1-((1S)-1-ethyl-2-hydroxyethyl)-6,7-bis(4-fluorophenyl)imidazo[4,5-b]pyridin-2-ol
6-chloro-7-(4-fluorophenyl)-1-[2-hydroxy-1-(2-methylpropyl)ethyl]imidazo[4,5-b]pyridin-2-ol
1-((1R)-1-ethyl-2-hydroxyethyl)-6-chloro-7-(4-fluorophenyl)imidazo[4,5-b]pyridin-2-ol
1-[(1S)-1-(methoxymethyl)propyl]-6-chloro-7-(4-fluorophenyl)imidazo[4,5-b]pyridin-2-ol
1-((1R)-1-ethyl-2-hydroxyethyl)-7-(3,4-difluorophenyl)-6-chloroimidazo[4,5-b]pyridin-2-ol
1-[(1R)-1-(methoxymethyl)propyl]-6-chloro-7-(4-fluorophenyl)imidazo[4,5-b]pyridin-2-ol
1-((1S)-1-ethyl-2-hydroxy-2-methylpropyl)-6-chloro-7-(4-fluorophenyl)imidazo[4,5-b]pyridin-2-ol
1-[(1R)-1-(methoxymethyl)propyl]-6-chloro-7-(5-fluoro(2-pyridyl))imidazo[4,5-b]pyridin-2-ol
6-chloro-1-(ethylpropyl)-7-(2-thienyl)imidazo[4,5-b]pyridin-2-ol
6-chloro-1-(ethylpropyl)-7-(3-thienyl)imidazo[4,5-b]pyridin-2-ol
6-chloro-7-(5-chloro(2-thienyl))-1-(ethylpropyl)imidazo[4,5-b]pyridin-2-ol
1-((1S)-1-ethyl-2-hydroxyethyl)-6-chloro-7-(2-thienyl)imidazo[4,5-b]pyridin-2-ol
1-((1S)-1-ethyl-2-hydroxyethyl)-6-chloro-7-(3-thienyl)imidazo[4,5-b]pyridin-2-ol
1-((1S)-1-ethyl-2-hydroxyethyl)-6-chloro-7-(5-chloro(2-thienyl))imidazo[4,5-b]pyridin-2-ol
6-chloro-7-(4-fluorophenyl)-1-(2-hydroxy-tert-butyl)imidazo[4,5-b]pyridin-2-ol
1-((1R)-1-ethyl-2-hydroxyethyl)-6-chloro-7-(5-fluoro(2-pyridyl))imidazo[4,5-b]pyridin-2-ol
1-((1S)-1-ethyl-2-hydroxyethyl)-7-(4-chlorophenyl)-6-fluoroimidazo[4,5-b]pyridin-2-ol
1-((1S)-1-ethyl-2-hydroxyethyl)-6-chloro-7-pyrazin-2-ylimidazo[4,5-b]pyridin-2-ol
1-((1S)-1-ethyl-2-hydroxyethyl)-6-fluoro-7-(4-fluorophenyl)imidazo[4,5-b]pyridin-2-ol
1-((1S)-1-ethyl-2-hydroxyethyl)-6-chloro-7-(5-fluoro(2-pyridyl))imidazo[4,5-b]pyridin-2-ol
1-((1R)-1-ethyl-2-hydroxy-2-methylpropyl)-6-chloro-7-(5-fluoro(2-pyridyl))imidazo[4,5-b]pyridin-2-ol
1-[(1S)-1-(methoxymethyl)propyl]-6-chloro-7-(5-fluoro(2-pyridyl))imidazo[4,5-b]pyridin-2-ol
1-((1S)-1-ethyl-2-hydroxy-2-methylpropyl)-6-chloro-7-(5-fluoro(2-pyridyl))imidazo[4,5-b]pyridin-2-ol
1-((1R)-1-ethyl-2-hydroxy-2-methylpropyl)-6-chloro-7-(4-fluorophenyl)imidazo[4,5-b]pyridin-2-ol
(2S)-2-[6-chloro-7-(4-fluorophenyl)-2-hydroxyimidazo[4,5-b]pyridinyl]butyl acetate
1-[(1S)-2-hydroxy-1-(2-methylpropyl)ethyl]-6-chloro-7-(4-fluorophenyl)imidazo[4,5-b]pyridin-2-ol
6-chloro-1-cyclopentyl-7-(4-fluorophenyl)imidazo[4,5-b]pyridin-2-ol
1-((1R)-2-amino-1-ethylethyl)-6-chloro-7-(4-fluorophenyl)imidazo[4,5-b]pyridin-2-ol
1-((1R)-2-amino-1-ethylethyl)-6-chloro-7-(5-fluoro(2-pyridyl))imidazo[4,5-b]pyridin-2-ol
N-{1(2S)-2-[6-chloro-7-(4-fluorophenyl)-2-hydroxyimidazo[4,5-b]pyridinyl]butyl}acetamide
1-((1S)-2-amino-1-ethylethyl)-6-chloro-7-(4-fluorophenyl)imidazo[4,5-b]pyridin-2-ol
1-((1S)-2-amino-1-ethylethyl)-6-chloro-7-(5-fluoro(2-pyridyl))imidazo[4,5-b]pyridin-2-ol
N{-1(2R)-2-[6-chloro-7-(4-fluorophenyl)-2-hydroxyimidazo[4,5-b]pyridinyl]butyl}acetamide
1-((1S)-1-ethyl-3-hydroxy-3-methylbutyl)-6-chloro-7-(4-fluorophenyl)imidazo[4,5-b]pyridin-2-ol
1-((1R)-1-ethyl-3-hydroxy-3-methylbutyl)-6-chloro-7-(4-fluorophenyl)imidazo[4,5-b]pyridin-2-ol
6-chloro-1-(ethylpropyl)-7-pyrazolylimidazo[4,5-b]pyridin-2-ol
2-{(1S)-1-[6-chloro-7-(4-fluorophenyl)-2-hydroxyimidazo[4,5-b]pyridinyl]propyl}propane-1,3-diol
6-chloro-1-(methylethyl)-7-pyrazolylimidazo[4,5-b]pyridin-2-ol
1-((1S)-1-ethyl-2-hydroxyethyl)-6-chloro-7-pyrazolylimidazo[4,5-b]pyridin-2-ol
6-chloro-1-(ethylpropyl)-7-(1-methylpyrazol-3-yl)imidazo[4,5-b]pyridin-2-ol
1-((1S)-1-methylpropyl)-6-chloroimidazo[4,5-b]pyridin-2-ol
1-((1R)-1-methylpropyl)-6-chloro-7-pyrazolylimidazo[4,5-b]pyridin-2-ol
1-((1S)-1-methylpropyl)-6-chloro-7-pyrazolylimidazo[4,5-b]pyridin-2-ol 6-chloro-1-[2-methoxy-1-(methoxymethyl)ethyl]-7-pyrazolylimidazo[4,5-b]pyridin-2-ol 6-chloro-1-(ethylpropyl)-7-imidazolylimidazo[4,5-b]pyridin-2-ol 1-((1R)-1-methylpropyl)-7-pyrazolylimidazo[4,5-b]pyridin-2-ol 6-chloro-1-(methylpropyl)-7-pyrazolylimidazo[4,5-b]pyridin-2-ol The chemical entities described herein can be synthesized utilizing techniques well known in the art, e.g., as illustrated below with reference to the Reaction Schemes.

Unless specified to the contrary, the reactions described herein take place at atmospheric pressure, generally within a temperature range from −10° C. to 200° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like]. Unless specified to the contrary, the solvents used in the reactions described herein are inert organic solvents. Unless specified to the contrary, for each gram of the limiting reagent, one cc (or mL) of solvent constitutes a volume equivalent Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Many of the optionally substituted starting compounds and other reactants are commercially available, e.g., from Aldrich Chemical Company (Milwaukee, Wis.) or can be readily prepared by those skilled in the art using commonly employed synthetic methodology.

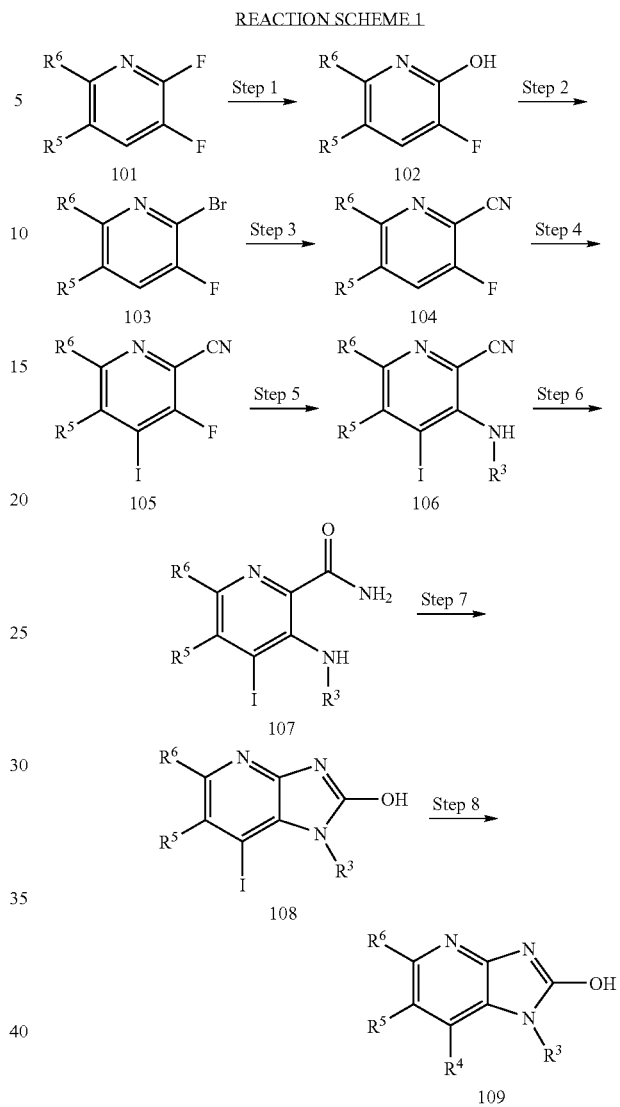

REACTION SCHEME 1

Referring to Reaction Scheme 1, step 1, a compound of Formula 101 is converted to the corresponding pyridin-2-ol through reflux with an excess, such as about four equiv., of sodium hydroxide in water. The product, a compound of Formula 102, is isolated and optionally purified.

Referring to Reaction Scheme 1, step 2, a compound of Formula 102 is converted to the corresponding 2-bromopyridine by reaction with phosphorous oxybromide in a solvent, such as DMF under heat, for example, about 130° C. The product, a compound of Formula 103, is isolated and optionally purified.

Referring to Reaction Scheme 1, step 3, a compound of Formula 103 is converted to the corresponding 2-cyanopyridine by reacting with a slight excess, such as about 1.25 eq., of CuCN in a solvent, such as DMSO, under heat, for example, about 120° C. The product, a compound of Formula 104, is isolated and optionally purified.

Referring to Reaction Scheme 1, step 4, a compound of Formula 104 is converted to the corresponding 4-iodopicolinonitrile by reaction with a slight excess, such as about 1.1 equiv., of a base, such as LDA, at low temperature, for example, about −78° C.; followed by addition of an excess, such as about 1.5 equiv., of iodine and subsequent warming to ambient temperature. The product, a compound of Formula 105, is isolated and optionally purified.

Referring to Reaction Scheme 1, step 5, a compound of Formula 105 is heated with an excess, such as about 10 equiv., of an appropriately substituted amine. The product, a compound of Formula 106, is isolated and optionally purified.

Referring to Reaction Scheme 1, step 6, a compound of Formula 106 is oxidized to the corresponding amide through addition of a base, for example, potassium carbonate in a solvent, such as DMSO, followed by cooling to about 0° C. and addition of aqueous hydrogen peroxide. The product, a compound of Formula 107, is isolated and optionally purified.

Referring to Reaction Scheme 1, step 7, a compound of Formula 107 is dissolved in methanol with a base, such as KOH, cooled, for example, to about −10° C., and iodosobenzenediacetate is added. The product, a compound of Formula 108, is isolated and optionally purified.

Referring to Reaction Scheme 1, step 8, a compound of Formula 108 is coupled to an appropriately substituted boronic acid, using a catalyst, such as (DPPF)PdCl$_2$, and a base, such as 2M K$_2$CO$_3$ in water, and subjecting the resulting mixture to a microwave reactor and heated, for example, to about 120° C. The product, a compound of Formula 109, is isolated and purified.

A racemic mixture is optionally placed on a chromatography column and separated into (R)- and (S)-enantiomers.

The compounds described herein are optionally contacted with a pharmaceutically acceptable acid to form the corresponding acid addition salts.

Pharmaceutically acceptable acid addition salts of compounds of Formula I are optionally contacted with a base to form the corresponding free base.

The chemical entities described herein modulate one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere, and are useful to bind to, inhibit and/or potentiate the activity thereof. As used in this context, "modulate" means either increasing or decreasing myosin activity, whereas "potentiate" means to increase activity and "inhibit" means to decrease activity.

Also provided are methods for enhancing skeletal muscle efficiency in a patient in need thereof, comprising administering to said patient an effective amount of at least one chemical entity that selectively binds the troponin complex of fast skeletal muscle fiber or sarcomere. In some embodiments, the chemical entity activates fast skeletal muscle fiber or sarcomere. In some embodiments, administration of the chemical entity results in an increase in skeletal muscle power output. In some embodiments, administration of the chemical entity results in increased sensitivity of the fast skeletal muscle fiber or sarcomere to calcium ion, as compared to skeletal muscle fiber or sarcomere untreated with the chemical entity. In some embodiments, administration of the chemical entity results in a lower concentration of calcium ions results in the binding of skeletal muscle myosin to actin. In some embodiments, administration of the at least one chemical entity results in the fast skeletal muscle fiber generating force more efficiently at submaximal levels of muscle contraction.

Also provided is a method for sensitizing a fast skeletal muscle fiber to produce force in response to lower concentrations of calcium ion, comprising contacting the fast skeletal muscle fiber with at least one chemical entity that selectively binds to troponin complex in fast skeletal muscle sarcomere.

In some embodiments, contacting the fast skeletal muscle fiber with the chemical entity results in activation of the fast skeletal muscle fiber at a lower calcium ion concentration than in an untreated fast skeletal muscle fiber. In some embodiments, contacting the fast skeletal muscle fiber with the chemical entity results in the production of increased force at a lower calcium ion concentration in comparison with an untreated fast skeletal muscle fiber.

Also provided is a method for increasing time to skeletal muscle fatigue in a patient in need thereof, comprising contacting fast skeletal muscle fiber with a compound that selectively binds to the troponin complex of the fast skeletal muscle fiber. In some embodiments, the compound binds to form a ligand-troponin complex-calcium ion complex that activates the fast skeletal muscle fiber. In some embodiments, formation of the complex and/or activation of the fast skeletal muscle fiber results in enhanced force and/or increased time to fatigue as compared to untreated fast skeletal muscle contacted with a similar calcium ion concentration The chemical entities, pharmaceutical compositions and methods described herein are capable of modulating the contractility of the skeletal sarcomere in vivo and can have application in both human and animal disease. Such chemical entities may, for example, be capable of increasing basal ATPase rate of skeletal myosin or may increase the power output of skeletal myosin. Modulation would be desirable in a number of conditions or diseases, including, but not limited to, neuromuscular disorders (e.g., ALS), conditions having muscle wasting (e.g., sarcopenia and cachexia syndromes), claudication, frailty, metabolic syndrome, muscle atrophy associated with disuse, muscle fatigue, muscle spasms, obesity, and other acute and chronic conditions and diseases.

More specifically, the chemical entities described herein may be useful for the treatment of epilepsy, Amyotrophic Lateral Sclerosis (ALS), myasthenia gravis, spinal muscular atrophy, multiple sclerosis (MS), and other neuromuscular conditions.

In addition, the treatment of muscular myopathies, such as muscular dystrophies are encompassed by the invention. Muscular dystrophy can be characterized by progressive muscle weakness, destruction and regeneration of the muscle fibers, and eventual replacement of the muscle fibers by fibrous and fatty connective tissue. There is no accumulation of metabolic storage material in the muscle fibers of patients suffering from muscular dystrophy. Treatment according to the invention may alleviate some of the symptoms of the disease and provide improved quality of life for the patients.

The chemical entities also will be useful for the treatment of frailty or sarcopenia associated with aging. More specifically, clinically, a decline in such skeletal muscle tissue mass, or muscle atrophy, is an important contributor to frailty in older individuals. In human males, muscle mass declines by one-third between the ages of 50 and 80. In older adults, extended hospitalization can result in further disuse atrophy leading to a potential loss of the ability for independent living and to a cascade of physical decline. Moreover, the physical aging process profoundly affects body composition, including significant reductions in lean body mass and increases in central adiposity. The changes in overall adiposity and fat distribution appear to be important factors in many common "age-related" diseases such as hypertension, glucose intolerance and diabetes, dyslipidemia, and atherosclerotic cardiovascular disease. In addition, it is possible that the age-associated decrement in muscle mass, and subsequently in strength and endurance, may be a critical determinant for functional loss, dependence and disability. Muscle weakness is also a major factor predisposing the elderly to falls and the resulting morbidity and mortality.

The chemical entities also may find use in the treatment of disuse atrophy, wasting or cachexia, diabetes, and the treatment of certain conditions associated with reductions in muscle mass of older-aged animals, such as muscle wasting associated with other diseases, including but not limited to hypertension, COPD, heart failure, chronic kidney disease, obesity, claudication, metabolic syndrome, chronic fatigue syndrome, diabetes, and atherosclerotic cardiovascular disease.

The chemical entities may also find use in the context of patients undergoing rehabilitation, including both patients in the hospital such as patients following surgery and patients undergoing longer term rehabilitation in an outpatient setting.

Methods to identify the chemical entities as binding to a protein or as a modulator of the binding characteristics or biological activity of a protein are described in, for example, U.S. Pat. No. 6,410,254 and U.S. patent application Ser. No. 10/987,165.

For example, test compounds can be assayed in a highly parallel fashion by using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

In some embodiments, the method uses a 384 well plate format and a 25 μL reaction volume. A pyruvate kinase/lactate dehydrogenase coupled enzyme system (Huang T G and Hackney D D. (1994) J Biol Chem 269(23):16493-501) can be used to measure the rate of ATP hydrolysis in each well. As will be appreciated by those in the art, the assay components are added in buffers and reagents. The incubation periods can be optimized to give adequate detection signals over the background. The assay can be done in real time giving the kinetics of ATP hydrolysis which increases the signal to noise ratio of the assay.

The compounds can be further tested using skinned muscle fiber preparations. Such assays are known in the art. See, e.g., Cheung et al. (2002) Nature Cell Biol. 4:83 and U.S. Patent Publication No. 20020006962.

The chemical entities described herein are administered at a therapeutically effective dosage, e.g., a dosage sufficient to provide treatment for the disease states previously described. While human dosage levels have yet to be optimized for the chemical entities described herein, generally, a daily dose ranges from about 0.05 to 100 mg/kg of body weight; in certain embodiments, from about 0.10 to 10.0 mg/kg of body weight, and in certain embodiments, from about 0.15 to 1.0 mg/kg of body weight. Thus, for administration to a 70 kg person, in certain embodiments, the dosage range would be about from 3.5 to 7000 mg per day; in certain embodiments, about from 7.0 to 700.0 mg per day, and in certain embodiments, about from 10.0 to 100.0 mg per day. The amount of the chemical entity administered will, of course, be dependent on the subject and disease state being treated, the severity of the affliction, the manner and schedule of administration and the judgment of the prescribing physician; for example, a likely dose range for oral administration would be from about 70 to 700 mg per day, whereas for intravenous administration a likely dose range would be from about 70 to 700 mg per day depending on compound pharmacokinetics.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarily, vaginally, rectally, or intraocularly. In some embodiments, oral or parenteral administration is used.

Pharmaceutically acceptable compositions include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium croscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see Remington's Pharmaceutical Sciences, Mack Publishing Company, Easton, Pa.

In addition, the chemical entities described herein can be co-administered with, and the pharmaceutical compositions can include, other medicinal agents, pharmaceutical agents, adjuvants, and the like. Suitable medicinal and pharmaceutical agents include modulators of one or more of skeletal myosin, skeletal actin, skeletal tropomyosin, skeletal troponin C, skeletal troponin I, skeletal troponin T, and skeletal muscle, including fragments and isoforms thereof, and the skeletal sarcomere and other suitable therapeutic agents useful in the treatment of the aforementioned disorders including: anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents, as well as the agents described in U.S. Patent Application No. 2005/0197367.

Suitable additional medicinal and pharmaceutical agents include, for example: orlistat, sibramine, diethylpropion, phentermine, benzaphetamine, phendimetrazine, estrogen, estradiol, levonorgestrel, norethindrone acetate, estradiol valerate, ethinyl estradiol, norgestimate, conjugated estrogens, esterified estrogens, medroxyprogesterone acetate, testosterone, insulin-derived growth factor, human growth hormone, riluzole, cannabidiol, prednisone, albuterol, non-steroidal anti-inflammatory drugs, and botulinum toxin.

Other suitable medicinal and pharmaceutical agents include TRH, diethylstilbesterol, theophylline, enkephalins, E series prostaglandins, compounds disclosed in U.S. Pat. No. 3,239,345 (e.g., zeranol), compounds disclosed in U.S. Pat. No. 4,036,979 (e.g., sulbenox), peptides disclosed in U.S. Pat. No. 4,411,890 growth hormone secretagogues such as GHRP-6, GHRP-1 (disclosed in U.S. Pat. No. 4,411,890 and publications WO 89/07110 and WO 89/07111), GHRP-2 (disclosed in WO 93/04081), NN703 (Novo Nordisk), LY444711 (Lilly), MK-677 (Merck), CP424391 (Pfizer) and B-HT920, growth hormone releasing factor and its analogs, growth hormone and its analogs and somatomedins including IGF-1 and IGF-2, alpha-adrenergic agonists, such as clonidine or serotonin 5-$HT_D$ agonists, such as sumatriptan, agents which inhibit somatostatin or its release, such as physostigmine, pyridostigmine, parathyroid hormone, PTH(1-34), and bisphosphonates, such as MK-217 (alendronate).

Still other suitable medicinal and pharmaceutical agents include estrogen, testosterone, selective estrogen receptor modulators, such as tamoxifen or raloxifene, other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999), and progesterone receptor agonists ("PRA"), such as levonorgestrel, medroxyprogesterone acetate (MPA).

Still other suitable medicinal and pharmaceutical agents include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer), other beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993, WO 99/00353, and GB98/284425, and anorectic agents, such as dexamphetamine, phentermine, phenylpropanolamine or mazindol.

Still other suitable medicinal and pharmaceutical agents include HIV and AIDS therapies, such as indinavir sulfate, saquinavir, saquinavir mesylate, ritonavir, lamivudine, zidovudine, lamivudine/zidovudine combinations, zalcitabine, didanosine, stavudine, and megestrol acetate.

Still other suitable medicinal and pharmaceutical agents include antiresorptive agents, hormone replacement therapies, vitamin D analogues, elemental calcium and calcium supplements, cathepsin K inhibitors, MMP inhibitors, vitronectin receptor antagonists, Src SH.sub.2 antagonists, vacular —$H^+$-ATPase inhibitors, ipriflavone, fluoride, Tibo lone, pro stanoids, 17-beta hydroxysteroid dehydrogenase inhibitors and Src kinase inhibitors.

The above other therapeutic agents, when employed in combination with the chemical entities described herein, may be used, for example, in those amounts indicated in the Physicians' Desk Reference (PDR) or as otherwise determined by one of ordinary skill in the art.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol and the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

EXAMPLES

The following examples serve to more fully describe the manner of using the above-described invention. It is understood that these examples in no way serve to limit the true scope of this invention, but rather are presented for illustrative purposes.

Example 1

Preparation of 6-Chloro-1-(pentan-3-yl)-7-phenyl-1H-imidazo[4,5-b]pyridin-2-ol

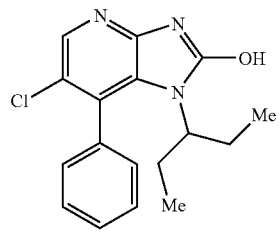

6-Chloro-1-(pentan-3-yl)-7-phenyl-1H-imidazo[4,5-b]pyridin-2-ol

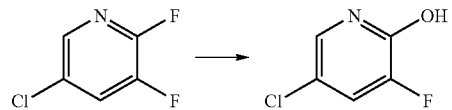

5-Chloro-3-fluoro-2-hydroxypyridine. To a solution of NaOH (101 g, 2.5 mol) in water (500 mL) was added 5-chloro-2,3-difluoropyridine (101 g, 0.68 mol) as a liquid, and the resulting mixture was heated to reflux overnight. After cooling to room temperature, the mixture was filtered through a pad of celite and the pH was adjusted to 1 by the addition of concentrated HCl. The resulting solid was dissolved in ethyl acetate. The combined organic layers were dried over sodium sulfate, filtered and concentrated in vacuo. The title compound was obtained as a white solid (78 g, 78%) and was used without additional purification. The product was characterized by $^1$H NMR.

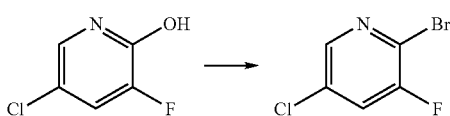

2-Bromo-5-chloro-3-fluoropyridine. To solid 5-chloro-3-fluoro-2-hydroxypyridine (75 g, 0.51 mmol) was added melted POBr$_3$ (150 g, 0.52 mmol). DMF (2 mL) was then added by pipet, and the mixture was heated at 130° C. for 1 h. The excess POBr$_3$ was quenched by the careful addition of water to the reaction mixture at 0° C., and the resulting mixture was dissolved in a 2:1 mixture of EtOAc:water. The organic layer was washed three times with water and once with brine, dried over sodium sulfate, filtered and concentrated in vacuo. The resulting yellow oil was passed through a plug of silica gel (10% Et$_2$O:90% hexanes) to provide the title compound as a white solid (79.4 g, 74%). The product was characterized by $^1$H NMR.

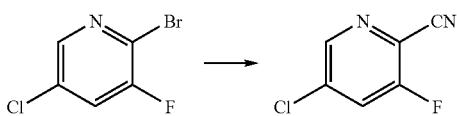

5-Chloro-3-fluoropicolinonitrile. 2-Bromo-5-chloro-3-fluoropyridine (107 g, 0.5 mmol) and CuCN (55 g, 0.62 mmol) were added to a round bottom flask with a magnetic stirbar. The flask was fitted with a septum and purged with nitrogen for 10 minutes. DMSO (430 mL) was then added by syringe and the resulting mixture stirred at 120° C. for 3 h. The reaction was cooled to room temperature and then poured into a vigorously stirred mixture of EtOAc (1 L) and brine (1 L). The organic layer was washed with water and brine, dried over sodium sulfate, filtered and concentrated in vacuo. Silica gel chromatography (15% ethyl ether, 85% hexanes) provided the title compound as an off-white solid (52 g, 67%). The product was characterized by $^1$H NMR.

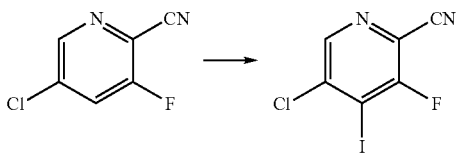

5-Chloro-3-fluoro-4-iodopicolinonitrile. To a cooled (−78° C.) solution of LDA (34.9 mmol, 1.1 equiv) in dry THF (200 mL) was added dropwise 5-chloro-3-fluoropicolinonitrile (5 g, 31.9 mmol) in dry THF (100 mL) over 15 min. The resulting mixture was stirred at −78° C. for an additional 15 min. A cooled (−78° C.) solution of iodine (12 g, 47 mmol, 1.5 equiv) in dry THF (72 mL) was poured rapidly into the reaction, and the resulting mixture was removed from the cold bath and stirred for 20 s. The reaction was then quenched by the addition of saturated aq. NaS$_2$O$_3$. The reaction mixture was diluted with ethyl acetate, and the organic layer was washed with brine, dried over sodium sulfate, filtered and concentrated in vacuo. Silica gel chromatography (5% EtOAc, 95% hexanes) provided the title compound as a yellow solid (7.4 g, 82%) which was characterized by $^1$HNMR.

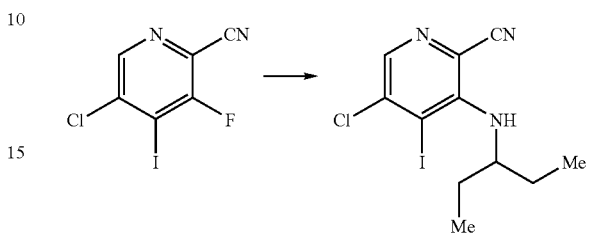

5-Chloro-4-iodo-3-(pentan-3-ylamino)picolinonitrile. A solution of 5-chloro-3-fluoro-4-iodopicolinonitrile (46 mg, 0.16 mmol) in 3-aminopentane (1 mL) was heated to 80° C. for 1 h. The reaction mixture was allowed to cool to RT, concentrated in vacuo, and then diluted with EtOAc and water. The organic layer was washed with water and filtered through a silica gel plug to provide the title compound as a white powder (55 mg, 100%) which was characterized by LCMS (m/z=350.1 [M+H]$^+$) and $^1$H NMR.

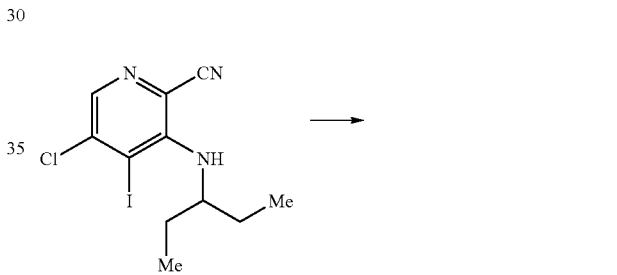

5-Chloro-4-iodo-3-(pentan-3-ylamino)picolinamide. To a solution of 5-chloro-4-iodo-3-(pentan-3-ylamino)picolinonitrile (55 mg, 0.16 mmol) in DMSO (1 mL) was added solid potassium carbonate (210 mg, 0.64 mmol). The mixture was cooled in an ice water bath (0° C.) and aqueous hydrogen peroxide (30%, 0.5 mL) was added. The reaction was allowed to warm to room temperature and monitored by LCMS. After the reaction was complete, the reaction mixture was diluted with EtOAc, and the organic layer was washed repeatedly with water. The organic layer was then dried over sodium sulfate, filtered and concentrated in vacuo. The residue was filtered through a silica gel plug to provide the title compound as a white solid (50 mg, 83%). The compound was characterized by LCMS (m/z=368.1 [M+H]$^+$) and $^1$H NMR.

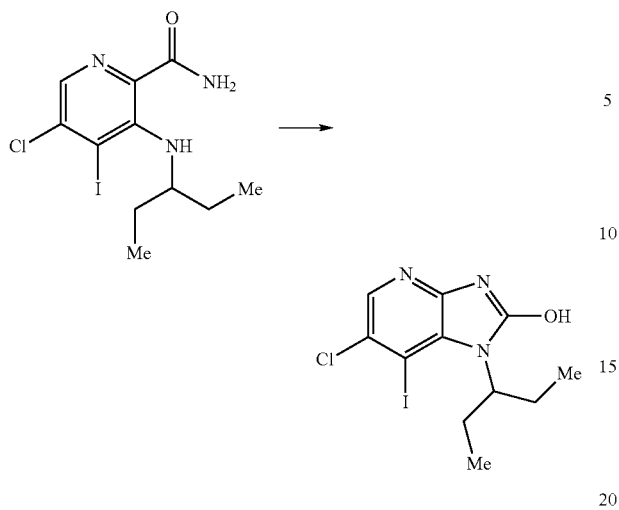

6-Chloro-7-iodo-1-(pentan-3-yl)-1H-imidazo[4,5-b]pyridin-2-ol. To a cooled (−10° C.) mixture of 5-chloro-4-iodo-3-(pentan-3-ylamino)picolinamide (50 mg, 0.13 mmol) and KOH (19 mg, 0.36 mmol) in MeOH (1 mL) was added iodosobenzenediacetate (44 mg, 0.14 mmol) as a solid. The reaction was allowed to warm to room temperature and stirred for 1 hour. The solvent was removed in vacuo, and the residue was dissolved in EtOAc and water. The pH of the aqueous layer was adjusted to pH 6 by the addition of 1 M HCl, and the organic layer was then removed, dried over sodium sulfate, filtered, and concentrated in vacuo. Silica gel chromatography (50% EtOAc, 50% hexanes) provided the title compound as a white solid (30 mg, 60%). The compound was characterized by LCMS (m/z=366.2 [M+H]$^+$) and $^1$H NMR.

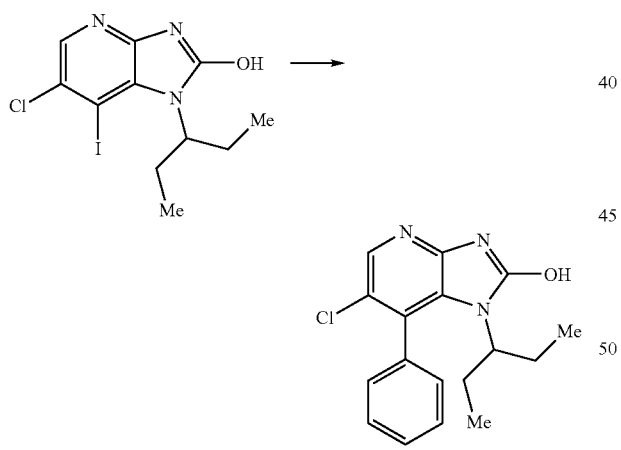

6-Chloro-1-(pentan-3-yl)-7-phenyl-1H-imidazo[4,5-b]pyridin-2-ol. 6-Chloro-7-iodo-1-(pentan-3-yl)-1H-imidazo[4,5-b]pyridin-2-ol (190 mg, 0.52 mmol), phenylboronic acid (76 mg, 0.63 mmol), and (DPPF)PdCl$_2$ (38 mg, 0.052 mmol) were added to a microwave vial equipped with stirbar. A septum was affixed to the vial and the vessel was purged with nitrogen for 5 min. Degassed dioxane (5 mL), and degassed 2 M K$_2$CO$_3$ (aq.) (1 mL, 2 mmol) were added by syringe, and the septum was replaced with a crimped vial cap. The reaction was heated to 135° C. for 20 min. The reaction mixture was diluted with EtOAc and water, and the organic layer was dried over sodium sulfate, filtered and concentrated in vacuo. Purification by preparative LCMS provided the title compound as a white solid (60 mg). The compound was characterized by LCMS (m/z=316.1 [M+H]$^+$) and $^1$H NMR.

Example 2

Preparation of ((R)-1-sec-Butyl-6-chloro-7-(1H-pyrazol-1-yl)-1H-imidazo[4,5-b]pyridin-2-ol)

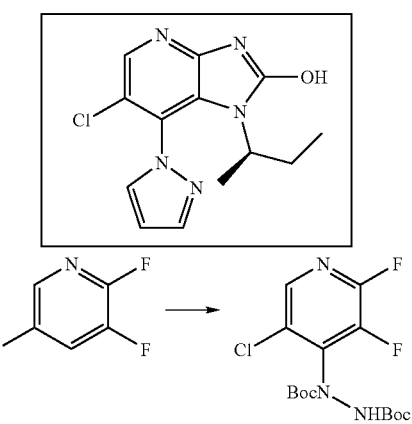

Di-tert-butyl 1-(5-chloro-2,3-difluoropyridin-4-yl)hydrazine-1,2-dicarboxylate. To a stirred solution of diisopropylamine (17 mL, 0.12 mol, 1.2 equiv) in THF (400 mL) at −78° C. under a nitrogen atmosphere was slowly added n-BuLi (11 mL, 10 M in hexane, 0.11 mol, 1.1 equiv). The mixture was stirred at −78° C. for an additional 30 minutes followed by the dropwise addition of 5-chloro-2,3-difluoropyridine (15 g, 0.10 mol, 1.0 equiv) in THF (40 mL). After stirring a further 45 minutes at −78° C., a solution of di-tert-butyl azadicarboxylate (28 g, 0.12 mol, 1.2 equiv) in THF (200 mL) was added slowly, maintaining the reaction temperature below −70° C. During the course of addition, the reaction mixture became a slurry that thickened as addition continued. After an extra 5 minutes of stirring, an excess of aqueous NaHCO$_3$ was added to quench the reaction. The product was extracted with EtOAc, and the organic fractions were dried over Na$_2$SO$_4$ and concentrated to dryness under vacuum. Purification over silica gel using a 5%-15% gradient of EtOAc/hexanes gave the desired product (18 g, 48%) as a light yellow viscous oil. m/z=380 [M+H]$^+$

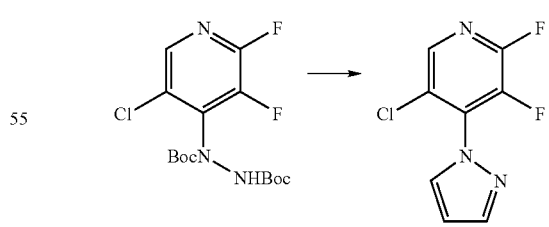

5-Chloro-2,3-difluoro-4-(1H-pyrazol-1-yl)pyridine. To a stirred mixture of di-tert-butyl 1-(5-chloro-2,3-difluoropyridin-4-yl)hydrazine-1,2-dicarboxylate (4.0 g, 0.010 mol, 1.0 equiv) and 1,1,3,3-tetramethoxypropane (17 mL, 0.10 mol, 10 equiv) was added a mixture of EtOH (100 mL) and concentrated H$_2$SO$_4$ (28 mL). The vessel was then sealed and heated to 45° C. After stirring for 45 minutes, the mixture was diluted with EtOAc (300 mL) and washed with water (300 mL), dried over Na$_2$SO$_4$ and concentrated under vacuum. The residue was purified over silica gel using 100% dichloromethane as eluent to give the desired product (1.6 g, 70%).

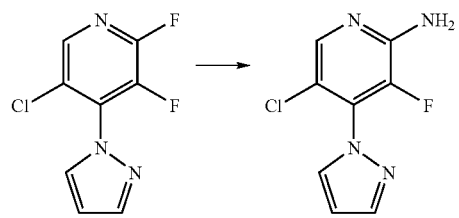

5-Chloro-3-fluoro-4-(1H-pyrazol-1-yl)pyridin-2-amine. A mixture of 5-chloro-2,3-difluoro-4-(1H-pyrazol-1-yl)pyridine (37 g, 0.17 mol, 1.0 equiv) and NMP (200 mL) in a pressure vessel was stirred at 50° C. under 20 psi of ammonia gas overnight. The mixture was diluted with water (400 mL) and extracted with EtOAc (2×300 mL). The organic fractions were combined, dried over Na$_2$SO$_4$, and concentrated under vacuum. To the residue was added water (300 mL) with stirring. The resulting solid was collected by filtration, and the cake was washed with isopropanol (100 mL) and dried under vacuum to give the desired product (24 g) as a yellow solid. The solid was recrystallized from isopropanol (40 mL) and EtOAc (20 mL) to give 19 g of pure product as an off white solid. The mother liquors were concentrated under vacuum and recrystallized from isopropanol (30 mL) to give another 5.1 g for a combined total of 24 g (67%) of desired product as an off white solid.

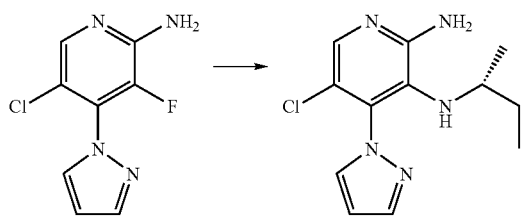

(R)—N-3-sec-Butyl-5-chloro-4-(1H-pyrazol-1-yl)pyridine-2,3-diamine. A mixture of 5-chloro-3-fluoro-4-(1H-pyrazol-1-yl)pyridin-2-amine (10 g, 0.047 mol, 1.0 equiv), (R)-sec-butylamine (10 g, 0.099 mol, 2 equiv) and NMP (40 mL) in a pressure vessel was stirred at 160° C. for 2 days. Another 5 g (0.045 mol, 1 equiv) of sec-butylamine was added and the mixture stirred at 160° C. for another 2 days. The solution was diluted with water and extracted with EtOAc. The organic fractions were dried over Na$_2$SO$_4$, and concentrated under vacuum until solid began to form. MTBE (~3 mL) was added and the mixture was allowed to stand at room temperature for 1 hour. The resulting solid was collected by filtration, washed with MTBE (~10 mL) and dried under vacuum to give the desired product (7.7 g, 62%).

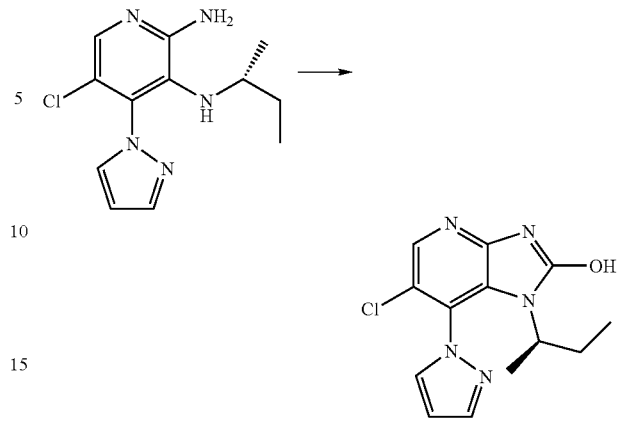

(R)-1-sec-Butyl-6-chloro-7-(1H-pyrazol-1-yl)-1H-imidazo[4,5-b]pyridin-2-ol. To a solution of (R)—N-3-sec-butyl-5-chloro-4-(1H-pyrazol-1-yl)pyridine-2,3-diamine (7.7 g, 0.029 mmol, 1.0 equiv) in THF (75 mL) was added carbonyldiimidazole (14 g, 0.086 mol, 3.0 equiv). The mixture was stirred at 60° C. overnight. After cooling to room temperature, the mixture was poured slowly into stirred 1 M HCl (400 mL). The resulting solids were collected by filtration, washed with MTBE and air dried under vacuum to give 7.3 g (86%) of pure desired product. m/z=292.1 [M+H]$^+$ Example 3

Preparation of Sarcomeric Proteins from Skeletal Muscle

Actin was purified by first preparing an ether powder of cardiac muscle (Zot H G and Potter J D. (1981) Preparative Biochemistry 11:381-395) as described below. Subsequently, actin was cycled between the filamentous and soluble state through rounds of centrifugation and dialysis (Spudich J A and Watt S. (1971) J. Biol. Chem. 246:4866-4871). It was stored in the filamentous state at 4° C.

Tropomyosin was extracted from the ether powder and separated from the other proteins based on pH dependent precipitations followed by successive ammonium sulfate cuts at 53% and 65% (Smillie L B. (1981) Methods Enzymol 85 Pt B:234-41). The troponins were isolated as an intact complex of TnC, TnT, and TnI. Ether powder is extracted in a high salt buffer. Successive ammonium sulfate cuts of 30% and 45% were done; the precipitate was solubilized by dialysis into a low salt buffer and then further purified on a DEAE Toyopearl column with a 25-350 mM KCl gradient. There was no measurable ATPase in any of the components except for myosin which naturally had a very low basal ATPase in the absence of actin.

Just prior to screening, the actin, tropomyosin, and troponin complex are mixed together in the desired ratio (e.g., 7:1:1) to achieve maximal calcium regulation of the actin filament. The screen is conducted at a pCa=6.5. This calcium concentration is in the physiological range during muscle contraction.

To measure the generation of ADP during the reaction, a pyruvate kinase/lactate dehydrogenase/NADH coupled enzyme system (PK/LDH) is added to the actin. The myosin is kept separately. The plates are read in real time so that kinetic curves are obtained. These compounds are in DMSO and were already spotted onto the bottoms of 384 well plates at 10 to 40 μg/ml final concentration.

Example 4

Actin Preparation

1. Extract powder (as prepared in Example 6 or 7 below) with 20 ml buffer A (see below, add BME and ATP just prior to use in each of the following steps) per gram of powder (200 ml per 10 g). Use a large 4 L beaker for 150 g of powder. Mix vigorously to dissolve powder. Stir at 4° C. for 30 min.
2. Separate extract from the hydrated powder by squeezing through several layers of cheesecloth. Cheesecloth should be pre-sterilized by microwaving damp for 1-2 min.
3. Re-extract the residue with the same volume of buffer A and combine extracts.
4. Spin in JLA10 rotor(s) for 1 hr at 10K rpm (4° C.). Collect supernatant through 2 layers of cheesecloth.
5. Add ATP to 0.2 mM and $MgCl_2$ to 50 mM. Stir on stir plate at 4° C. for 60 minutes to allow actin to polymerize/form para-crystals.
6. Slowly add solid KCl to 0.6 M (45 g/l). Stir at 4° C. for 30 min.
7. Spin in JLA10 rotor(s) at 10K rpm for 1 hr.
8. Depolymerization: Quickly rinse surface of pellets with buffer A and dispose of wash. Soften the pellets by pre-incubation on ice with small amount of buffer A in each tube (use less than half of final resuspension volume total in all tubes). Resuspend by hand first with cell scraper and combine pellets. Wash tubes with extra buffer using a 25 ml pipette and motorized pipettor, aggressively removing actin from sides of tubes. Homogenize in large dounce in cold buffer A on ice. Use 3 ml per gram of powder originally extracted.
9. Dialyze against buffer A with 4 changes over 48 hour period.
10. Collect dialyzed actin and spin in the 45Ti rotor at 40K rpm for 1.5 hr (4° C.).
11. Collect supernatant (G-Actin). Save a sample for gel analysis and determination of protein concentration.

To polymerize G-actin for storage add KCl to 50 mM (from 3 M stock), $MgCl_2$ to 1 mM, and $NaN_3$ to 0.02% (from 10% stock). Store at 4° C. Do not freeze.

Buffer A: 2 mM tris/HCl, 0.2 mM $CaCl_2$, 0.5 mM (36 µl/L) 2-mercaptoethanol, 0.2 mM $Na_2$ ATP (added fresh), and 0.005% Na-azide; pH 8.0.

Example 5

Powder Preparation

1. Volumes are given per about 1000 g of the minced muscle.
2. Pre-cut and boil cheesecloth for 10 min in water. Drain and dry.
3. Mince chicken breast in a prechilled meat grinder.
4. Extract with stirring in 2 L of 0.1 M KCl, 0.15 M K-phosphate, pH 6.5 for 10 min at 4° C. Spin 5000 rpm, 10 min, 4° C. in JLA. Collect the pellet.
5. Extract pellets with stirring with 2 L of 0.05 M $NaHCO_3$ for 5 min. Spin 5000 rpm, 10 min, 4° C. in JLA. Collect the pellet. Repeat the extraction once more.
6. Extract the filtered residue with 2 L of 1 mM EDTA, pH 7.0 for 10 min with stirring.
7. Extract with 2 L of $H_2O$ for 5 min with stirring. Spin 10000 rpm, 15 min, 4° C. in JLA. Carefully collect the pellet, part of which will be loose and gelatinous.
8. Extract 5 times with acetone (2 L of acetone for 10 min each with stirring). Squeeze through cheesecloth gently. All acetone extractions are performed at room temperature. Acetone should be prechilled to 4° C.
9. Drying: Place the filtered residue spread on a cheesecloth in a large glass tray and leave in a hood overnight. When the residue is dry, put in a wide mouth plastic bottle and store at 20° C.

Example 6

Alternate Powder Preparation

Based on Zot & Potter (1981) Prep. Biochem. 11 (4) pp. 381-395.

1. Dissect left ventricles of the cardiac muscle. Remove as much of the pericardial tissue and fat as possible. Grind in a prechilled meat grinder. Weigh.
2. Prepare 5 volumes of Extract buffer (see below). Be sure the pH=8.0. Then, homogenize the meat in a blender, 4 times 15 sec on blend with 15 secs in between. Do this with 1 volume weight/volume) of buffer taken from the 5 volumes already prepared. Add the homogenate back to the extract buffer and stir until well mixed (5 minutes).
3. Filter through one layer of cheesecloth in large polypropylene strainer. Resuspend back into 5 volumes of extract buffer as above.
4. Repeat Step 3 four more times. At the end, do not resuspend in extraction buffer but proceed to Step 5. The pellets should be yellow white.
5. Resuspend in 3 volumes (according to original weight) of 95% cold ethanol. Stir for 5 min and squeeze through cheesecloth as above, repeat two more times.
6. Weigh squeezed residue and then resuspend in 3 volumes (new weight/volume) of cold diethyl ether.
7. Repeat Step 6a total of three times.
8. Leave overnight in a single layer on a cheesecloth in a glass tray.
9. When dry, collect the powder, weigh and store in a wide-mouth jar at 4° C.

EXTRACT BUFFER: 50 mM KCl, 5 mM Tris pH 8.0
Prepare as 50 times concentrate:
For 2 L
250 mM Tris pH 8.0. Tris Base (121.14 g/mol, 60.6 g)
pH to 8.0 with conc. HCl, then add:
2.5 M KCl (74.55 g/mol, 372 g)

Example 7

Purification of Skeletal Muscle Myosin

See, Margossian, S. S, and Lowey, S. (1982) Methods Enzymol. 85, 55-123 and Goldmann, W. H. and Geeves, M. A. (1991) Anal. Biochem. 192, 55-58.
Solution A: 0.3 M KCl, 0.15 M potassium phosphate, 0.02 M EDTA, 0.005 M $MgCl_2$, 0.001 M ATP, pH 6.5.
Solution B: 1 M KCl, 0.025 M EDTA, 0.06 M potassium phosphate, pH 6.5.
Solution C, 0.6 M KCl, 0.025 M potassium phosphate, pH 6.5.
Solution D: 0.6 M KCl, 0.05 M potassium phosphate, pH 6.5.
Solution E: 0.15 M potassium phosphate, 0.01 M EDTA, pH 7.5.
Solution F: 0.04 M KCl, 0.01 M potassium phosphate, 0.001 M DTT, pH 6.5.
Solution G: 3 M KCl, 0.01 M potassium phosphate, pH 6.5.
All procedures are carried out at 4° C.

1. Obtain ~1000 g skeletal muscle, such as rabbit skeletal muscle.
2. Grind twice; extract with 2 L solution A for 15 min while stirring; add 4 L cold $H_2O$, filter through gauze; dilute with cold $H_2O$ to ionic strength of 0.04, (about 10-fold); let settle for 3 h; collect precipitate at 7,000 rpm in GSA rotor for 15 min.
3. Disperse pellet in 220 ml solution B; dialyze overnight against 6 L solution C; slowly add ~400 ml equal volume cold distilled $H_2O$; stir for 30 min; centrifuge at 10,000 rpm for 10 min in GSA rotor.
4. Centrifuge supernatant at 19,000 rpm for 1 h.
5. Dilute supernatant to ionic strength of 0.04 (~8-fold); let myosin settle overnight; collect about 5-6 L fluffy myosin precipitate by centrifuging at 10,000 rpm for 10 min in GSA rotor.
6. Resuspend pellet in minimal volume of solution G; dialyze overnight against 2 L solution D; centrifuge at 19,000 rpm for 2 h, in cellulose nitrate tubes; puncture tubes and separate myosin from fat and insoluble pellet.
7. Dilute supernatant to 5-10 mg/ml and dialyze against solution E extensively, load onto DEAE-sephadex column.
8. Preequilibrate with solution E; apply 500-600 g myosin at 30 ml/h; wash with 350 ml solution E; elute with linear gradient of 0-0.5 M KCl in solution E (2×1 liter); collect 10 ml fractions; pool myosin fractions (>0.1 M KCl); concentrate by overnight dialysis against solution F; centrifuge at 25,000 rpm for 30 min; store as above.
9. The myosin is then cut with chymotrypsin or papain in the presence of EDTA to generate the S1 fragment which is soluble at the low salt conditions optimal for ATPase activity (Margossian supra).

Example 8

Activation of Fast Skeletal Muscle Fibers

Fast fiber activators were identified by measuring the enzymatic activity of muscle myofibril preparations using the proprietary PUMA™ (see, e.g., U.S. Pat. Nos. 6,410,254, 6,743,599, 7,202,051, and 7,378,254) assay system. Myofibril preparations consisted of rabbit skeletal muscle (approximately 90% fast fibers) that had been treated with a detergen (triton X-100) to remove cellular membranes and then homogenized. This preparation retained all of the sarcomeric components in a native conformation and the enzymatic activity was still regulated by calcium. Compounds were tested using a myofibril suspension and a level of calcium sufficient to increase enzymatic activity of the myofibrils to 25% of their maximal rate (termed pCa25%). Enzymatic activity was tracked via a kinetic assay with a UV absorption readout. Hits were identified as compounds that increased the rate of enzymatic activity by greater than 40% at 40 μM. Myofibril preparations are calcium regulated and were screened at a level of calcium sufficient to produce a 25% increase in enzymatic rate. Detergent treated myofibrils were incubated with 500 μM ATP and 40 μM compound and a kinetic read of UV absorbance performed. Data was normalized to control wells.

Example 9

Using procedures similar to those described herein, the compounds in the following table were synthesized and tested.

| Name | M/Z (M + H unless noted) | AC1.4 Median |
|---|---|---|
| 1-[(1S)-2-hydroxy-1-(2-methylpropyl)ethyl]-6-chloro-7-(4-fluorophenyl)imidazo[4,5-b]pyridin-2-ol | 364.1 | 0.072† |
| 6-chloro-7-(4-chlorophenyl)-1-(ethylpropyl)imidazo[4,5-b]pyridin-2-ol | 351.0; 350.0 | 0.074† |
| 6-chloro-1-(ethylpropyl)-7-(4-fluorophenyl)imidazo[4,5-b]pyridin-2-ol | 334.0 | 0.074† |
| 6-chloro-7-(5-chloro(2-thienyl))-1-(ethylpropyl)imidazo[4,5-b]pyridin-2-ol | 354.0 [M − H] | 0.084† |
| 6-chloro-7-(4-fluorophenyl)-1-(methylethyl)imidazo[4,5-b]pyridin-2-ol | 306.0 | 0.096† |
| 7-(3,4-difluorophenyl)-6-chloro-1-(ethylpropyl)imidazo[4,5-b]pyridin-2-ol | 352.1 | 0.106† |
| 6-chloro-1-(ethylpropyl)-7-phenylimidazo[4,5-b]pyridin-2-ol | 316.0 | 0.110† |
| 6-chloro-7-(4-chloro-3-fluorophenyl)-1-(ethylpropyl)imidazo[4,5-b]pyridin-2-ol | 368.30 | 0.116† |
| 6-chloro-1-(ethylpropyl)-7-(3-thienyl)imidazo[4,5-b]pyridin-2-ol | 320.0 [M − H] | 0.124† |
| 6-chloro-1-(ethylpropyl)-7-(2-thienyl)imidazo[4,5-b]pyridin-2-ol | 320.0 [M − H] | 0.136† |
| 1-((1S)-1-ethyl-2-hydroxyethyl)-6-chloro-7-(5-chloro(2-thienyl))imidazo[4,5-b]pyridin-2-ol | 356.0 [M − H] | 0.178† |
| 1-(tert-butyl)-6-chloro-7-(4-fluorophenyl)imidazo[4,5-b]pyridin-2-ol | 320.3 | 0.199† |
| 6-chloro-7-(4-fluorophenyl)-1-[2-hydroxy-1-(2-methylpropyl)ethyl]imidazo[4,5-b]pyridin-2-ol | 364.1 | 0.210 |
| 6-chloro-1-(ethylpropyl)-7-(2-fluorophenyl)imidazo[4,5-b]pyridin-2-ol | 334 | 0.230† |
| (2S)-2-[6-chloro-7-(4-fluorophenyl)-2-hydroxyimidazo[4,5-b]pyridinyl]butyl acetate | 378.0 | 0.234† |
| 6-chloro-1-(ethylpropyl)-7-(3-fluorophenyl)imidazo[4,5-b]pyridin-2-ol | 334.0 | 0.248† |
| 1-[(1R)-1-(methoxymethyl)propyl]-6-chloro-7-(4-fluorophenyl)imidazo[4,5-b]pyridin-2-ol | 349.8 | 0.249 |
| 1-((1S)-1-ethyl-2-hydroxyethyl)-6-chloro-7-(4-chlorophenyl)imidazo[4,5-b]pyridin-2-ol | 352.0 | 0.261† |
| 6-chloro-1-(ethylpropyl)-7-(5-fluoro(2-pyridyl))imidazo[4,5-b]pyridin-2-ol | 335.0 | 0.268† |
| 6-chloro-1-(ethylpropyl)-7-[4-(trifluoromethyl)phenyl]imidazo[4,5-b]pyridin-2-ol | 384.1 | 0.274† |
| 1-[(1S)-1-(methoxymethyl)propyl]-6-chloro-7-(4-fluorophenyl)imidazo[4,5-b]pyridin-2-ol | 349.8 | 0.317 |
| 6-chloro-7-(5-chloro(2-pyridyl))-1-(ethylpropyl)imidazo[4,5-b]pyridin-2-ol | 351.0 | 0.320† |
| 1-((1S)-1-ethyl-2-hydroxy-2-methylpropyl)-6-chloro-7-(4-fluorophenyl)imidazo[4,5-b]pyridin-2-ol | 409.0; 364.0 | 0.320† |
| 6-chloro-7-(3-chlorophenyl)-1-(ethylpropyl)imidazo[4,5-b]pyridin-2-ol | 350.0 | 0.330† |

-continued

| Name | M/Z (M + H unless noted) | AC1.4 Median |
|---|---|---|
| 6-chloro-1-(ethylpropyl)-7-(4-methylphenyl)imidazo[4,5-b]pyridin-2-ol | 330.1 | 0.336† |
| 1-(1S)-1-ethyl-2-hydroxyethyl)-6-chloro-7-(4-fluorophenyl)imidazo[4,5-b]pyridin-2-ol | 336.1 | 0.363† |
| 4-[6-chloro-1-(ethylpropyl)-2-hydroxyimidazo[4,5-b]pyridin-7-yl]benzenecarbonitrile | 341.0 | 0.405† |
| 4-(6-chloro-2-hydroxy-1-(pentan-3-yl)-1H-imidazo[4,5-b]pyridin-7-yl)-2-fluorobenzonitrile | 358.8 | 0.458† |
| 1-((1S)-1-ethyl-3-hydroxypropyl)-6-chloro-7-(4-fluorophenyl)imidazo[4,5-b]pyridin-2-ol | 348.1; 350.0 | 0.475† |
| 6-chloro-1-(ethylpropyl)-7-(3-methylphenyl)imidazo[4,5-b]pyridin-2-ol | 330.1 | 0.482 |
| 1-((1R)-1-ethyl-2-hydroxy-2-methylpropyl)-6-chloro-7-(4-fluorophenyl)imidazo[4,5-b]pyridin-2-ol | 364.0 | 0.537 |
| 6-chloro-1-(ethylpropyl)-7-(6-methoxy(2-pyridyl))imidazo[4,5-b]pyridin-2-ol | 347.1 | 0.562† |
| 6-chloro-7-(2-chloro-4-methylphenyl)-1-(ethylpropyl)imidazo[4,5-b]pyridin-2-ol | 365.0 | 0.587 |
| 1-((1S)-1-ethyl-2-hydroxyethyl)-7-(3,4-difluorophenyl)-6-chloroimidazo[4,5-b]pyridin-2-ol | 354.1 | 0.707 |
| 6-chloro-1-(ethylpropyl)-7-(4-methoxyphenyl)imidazo[4,5-b]pyridin-2-ol | 346.1 | 0.728 |
| 6-chloro-7-(4-fluorophenyl)-1-(2-hydroxy-tert-butyl)imidazo[4,5-b]pyridin-2-ol | 334.3 [M − H] | 0.760 |
| 6-chloro-1-(ethylpropyl)-7-[4-(trifluoromethoxy)phenyl]imidazo[4,5-b]pyridin-2-ol | 400.0 | 0.781 |
| 1-((1S)-1-ethyl-2-hydroxyethyl)-6-chloro-7-(3-thienyl)imidazo[4,5-b]pyridin-2-ol | 322.0 [M − H] | 0.827 |
| 6-chloro-1-(ethylpropyl)-7-(2-fluoro-4-methoxyphenyl)imidazo[4,5-b]pyridin-2-ol | 364.1 | 0.942 |
| 1-[(1R)-1-(methoxymethyl)propyl]-6-chloro-7-(5-fluoro(2-pyridyl))imidazo[4,5-b]pyridin-2-ol | 396.0 | 1.142 |
| 1-((1S)-2-hydroxy-isopropyl)-6-chloro-7-(4-chlorophenyl)imidazo[4,5-b]pyridin-2-ol | 380.1 | 1.260 |
| 1-((1S)-1-ethyl-2-hydroxyethyl)-6-chloro-7-(2-thienyl)imidazo[4,5-b]pyridin-2-ol | 322.0 [M − H] | 1.349 |
| 1-((1S)-1-ethyl-2-hydroxyethyl)-6-chloro-7-phenylimidazo[4,5-b]pyridin-2-ol | 318.0; 352.0 | 1.474 |
| 6-chloro-1-(ethylpropyl)-7-(2-pyridyl)imidazo[4,5-b]pyridin-2-ol | 317.0 | 1.616 |
| 6-chloro-1-cyclopentyl-7-(4-fluorophenyl)imidazo[4,5-b]pyridin-2-ol | 332.1 | 1.677 |
| 6-chloro-1-(ethylpropyl)-7-(2-methylphenyl)imidazo[4,5-b]pyridin-2-ol | 328.0 | 1.688 |
| 2-[6-chloro-1-(ethylpropyl)-2-hydroxyimidazo[4,5-b]pyridin-7-yl]benzaldehyde | 343.0 | 1.689 |
| 6-chloro-1-(ethylpropyl)-7-(3-fluoro(4-pyridyl))imidazo[4,5-b]pyridin-2-ol | 335.1 | 1.709 |
| 6-chloro-7-(5-chloro(2-pyridyl))-1-(methylethyl)imidazo[4,5-b]pyridin-2-ol | 323.0 | 1.781 |
| 6-chloro-7-(2-chloro-4-methoxyphenyl)-1-(ethylpropyl)imidazo[4,5-b]pyridin-2-ol | 381.1 | 1.898 |
| 6-chloro-7-(5-chloro(3-pyridyl))-1-(ethylpropyl)imidazo[4,5-b]pyridin-2-ol | 351.0 | 1.899 |
| 3-[6-chloro-1-(ethylpropyl)-2-hydroxyimidazo[4,5-b]pyridin-7-yl]benzaldehyde | 343.0 | 1.943 |
| 6-chloro-7-(4-fluorophenyl)-1-prop-2-enylimidazo[4,5-b]pyridin-2-ol | 302.0 [M − H] | 1.947 |
| 1-((1R)-2-hydroxy-isopropyl)-6-chloro-7-(4-fluorophenyl)imidazo[4,5-b]pyridin-2-ol | 322.0 | 11.044 |
| 6-chloro-1-(ethylpropyl)-7-(4-methyl(2-pyridyl))imidazo[4,5-b]pyridin-2-ol | 331.0 | 11.301 |
| 6-chloro-1-(ethylpropyl)-7-(6-methyl(3-pyridyl))imidazo[4,5-b]pyridin-2-ol | 331.1 | 12.164 |
| 6-chloro-7-(4-fluorophenyl)-1-methylimidazo[4,5-b]pyridin-2-ol | 276.0 [M − H] | 12.620 |
| 6-chloro-1-(ethylpropyl)-7-(2-methyl(4-pyridyl))imidazo[4,5-b]pyridin-2-ol | 331.1 | 14.091 |
| 6-chloro-1-(ethylpropyl)-7-[3-(hydroxymethyl)phenyl]imidazo[4,5-b]pyridin-2-ol | 345.0 | 14.377 |
| 1-((1S)-1-ethyl-2-hydroxyethyl)-6,7-bis(4-fluorophenyl)imidazo[4,5-b]pyridin-2-ol | 396.1 | 17.720 |
| 6-chloro-1-(ethylpropyl)-7-(1-methylpyrazol-4-yl)imidazo[4,5-b]pyridin-2-ol | 320.1 | 17.805 |
| 6-chloro-1-(ethylpropyl)-7-(5-methylpyrimidin-2-yl)imidazo[4,5-b]pyridin-2-ol | 330.0 [M − H] | 18.694 |
| 6-chloro-1-(ethylpropyl)-7-(3-methoxyphenyl)imidazo[4,5-b]pyridin-2-ol | 306.0 | 2.001 |
| 1-((1S)-2-hydroxy-isopropyl)-6-chloro-7-(4-fluorophenyl)imidazo[4,5-b]pyridin-2-ol | 322.0 | 2.016 |
| 1-((1S)-1-ethyl-2-hydroxyethyl)-6-chloro-7-(4-chlorophenyl)imidazo[4,5-b]pyridin-2-ol | 352.0 | 2.059 |
| 1-(ethylpropyl)-7-phenylimidazo[4,5-b]pyridin-2-ol | 282.1 | 2.083 |
| 6-chloro-1-(ethylpropyl)-7-(3-fluoro-4-methoxyphenyl)imidazo[4,5-b]pyridin-2-ol | 364.2 | 2.102 |
| 1-((1S)-1-ethyl-2-hydroxyethyl)-6-chloro-7-(4-methylphenyl)imidazo[4,5-b]pyridin-2-ol | 330.0 [M − H] | 2.194 |
| 6-chloro-1-(ethylpropyl)-7-(6-methoxy(3-pyridyl))imidazo[4,5-b]pyridin-2-ol | 347.3 | 2.232 |
| 1-((1S)-3-hydroxy-1-methylpropyl)-6-chloro-7-(4-fluorophenyl)imidazo[4,5-b]pyridin-2-ol | 334.0 [M − H] | 2.309 |
| 6-chloro-7-(5-fluoro(2-pyridyl))-1-(methylethyl)imidazo[4,5-b]pyridin-2-ol | 307.0 | 2.323 |

-continued

| Name | M/Z (M + H unless noted) | AC1.4 Median |
|---|---|---|
| 1-((1R)-1-ethyl-2-hydroxyethyl)-6-chloro-7-(4-fluorophenyl)imidazo[4,5-b]pyridin-2-ol | 336.1 | 2.367 |
| 6-chloro-1-(ethylpropyl)-7-[3-(trifluoromethoxy)phenyl]imidazo[4,5-b]pyridin-2-ol | 400.1 | 2.369 |
| 1-((1R)-1-ethyl-3-hydroxypropyl)-6-chloro-7-(4-fluorophenyl)imidazo[4,5-b]pyridin-2-ol | 348.1 [M − H] | 2.547 |
| 1-((1S)-1-ethyl-2-hydroxyethyl)-7-(4-chlorophenyl)-6-fluoroimidazo[4,5-b]pyridin-2-ol | 336.1 | 2.643 |
| 6-chloro-1-(ethylpropyl)-7-(2-methoxy(4-pyridyl))imidazo[4,5-b]pyridin-2-ol | 347.1 | 2.808 |
| 2-[6-chloro-1-(ethylpropyl)-2-hydroxyimidazo[4,5-b]pyridin-7-yl]benzenecarbonitrile | 341.0 | 2.886 |
| 6-[6-chloro-1-(ethylpropyl)-2-hydroxyimidazo[4,5-b]pyridin-7-yl]pyridine-3-carbonitrile | 340.1 [M − H] | 2.892 |
| 6-chloro-1-(ethylpropyl)-7-(1-methyl(1H-indazol-6-yl))imidazo[4,5-b]pyridin-2-ol | 370.1 | 20.233 |
| {3-[6-chloro-1-(ethylpropyl)-2-hydroxyimidazo[4,5-b]pyridin-7-yl]phenyl}-N,N-dimethylcarboxamide | 386.0 | 21.245 |
| {4-[6-chloro-1-(ethylpropyl)-2-hydroxyimidazo[4,5-b]pyridin-7-yl]phenyl}(methylsulfonyl)amine | 409.1 | 26.368 |
| 6-chloro-1-(ethylpropyl)-7-pyrazol-3-ylimidazo[4,5-b]pyridin-2-ol | 306.1 | 26.881 |
| N-{4-[6-chloro-1-(ethylpropyl)-2-hydroxyimidazo[4,5-b]pyridin-7-yl]phenyl}acetamide | 373.2 | 28.930 |
| 6-chloro-1-(ethylpropyl)-7-(4-pyridyl)imidazo[4,5-b]pyridin-2-ol | 317.0 | 3.015 |
| 6-chloro-1-(ethylpropyl)-7-(3-hydroxyphenyl)imidazo[4,5-b]pyridin-2-ol | 332.1 | 3.021 |
| 4-[1-((1S)-1-ethyl-2-hydroxyethyl)-6-chloro-2-hydroxyimidazo[4,5-b]pyridin-7-yl]benzenecarbonitrile | 341.0 [M − H] | 3.249 |
| 3-[6-chloro-1-(ethylpropyl)-2-hydroxyimidazo[4,5-b]pyridin-7-yl]benzenecarbonitrile | 341.0 | 3.336 |
| (2S)-2-[6-chloro-7-(4-fluorophenyl)-2-hydroxyimidazo[4,5-b]pyridinyl]butyl (2S)-2-amino-3-methylbutanoate | 435.2 | 3.359 |
| 6-chloro-1-(ethylpropyl)-7-[2-(methoxymethyl)phenyl]imidazo[4,5-b]pyridin-2-ol | 359.8 | 3.588 |
| 6-chloro-1-(ethylpropyl)-7-[2-(trifluoromethyl)(4-pyridyl)]imidazo[4,5-b]pyridin-2-ol | 385.1 | 3.590 |
| 1-[(1S)-1-(methoxymethyl)propyl]-6-chloro-7-(5-fluoro(2-pyridyl))imidazo[4,5-b]pyridin-2-ol | 396.0 | 3.771 |
| 2-[6-chloro-1-(ethylpropyl)-2-hydroxyimidazo[4,5-b]pyridin-7-yl]benzoic acid | 358.0; 359.0 | 30.881 |
| (2S)-2-[6-chloro-7-(4-fluorophenyl)-2-hydroxyimidazo[4,5-b]pyridinyl]butyl dihydrogen phosphate | 457.0 | 31.644 |
| 6-chloro-1-(2-hydroxyethyl)-7-phenylimidazo[4,5-b]pyridin-2-ol | 290.0 | 34.551 |
| 6-chloro-1-(ethylpropyl)-7-[4-(methoxymethyl)phenyl]imidazo[4,5-b]pyridin-2-ol | 360.1 | 34.746 |
| 2-[6-chloro-1-(ethylpropyl)-2-hydroxyimidazo[4,5-b]pyridin-7-yl]benzamide | 359.0 | 36.169 |
| 1-[6-chloro-1-(ethylpropyl)-2-hydroxyimidazo[4,5-b]pyridin-7-yl]-3-(methylsulfonyl)benzene | 393.0 | 38.633 |
| 6-chloro-1-(ethylpropyl)-7-pyrazol-4-ylimidazo[4,5-b]pyridin-2-ol | 306.1 | 38.791 |
| 6-chloro-1-(ethylpropyl)-7-(5-methyl(1,2,4-oxadiazol-3-yl))imidazo[4,5-b]pyridin-2-ol | 322.1 | 4.017 |
| 1-((1R)-1-ethyl-2-hydroxyethyl)-7-(3,4-difluorophenyl)-6-chloroimidazo[4,5-b]pyridin-2-ol | 354.0 | 4.034 |
| 6-chloro-1-(ethylpropyl)-7-(6-methyl(2-pyridyl))imidazo[4,5-b]pyridin-2-ol | 331.0 | 4.048 |
| 1-((1S)-1-ethyl-2-hydroxyethyl)-6-fluoro-7-(4-fluorophenyl)imidazo[4,5-b]pyridin-2-ol | 320.1 | 4.204 |
| 7-(1H-indazol-6-yl)-6-chloro-1-(ethylpropyl)imidazo[4,5-b]pyridin-2-ol | 356.1 | 4.216 |
| 6-chloro-1-(ethylpropyl)-7-(5-fluoro(3-pyridyl))imidazo[4,5-b]pyridin-2-ol | 335.1 | 4.428 |
| 6-chloro-7-(3-chloro(4-pyridyl))-1-(ethylpropyl)imidazo[4,5-b]pyridin-2-ol | 351.3 | 4.471 |
| 1-((1S)-1-ethyl-2-hydroxyethyl)-6-chloro-7-pyrazin-2-ylimidazo[4,5-b]pyridin-2-ol | 318.0 | 40.701 |
| (tert-butoxy)-N-{4-[6-chloro-1-(ethylpropyl)-2-hydroxyimidazo[4,5-b]pyridin-7-yl]phenyl}-N-methylcarboxamide | 445.1 | 42.343 |
| 2-[7-(3,4-difluorophenyl)-6-chloro-2-hydroxyimidazo[4,5-b]pyridinyl]butyl dihydrogen phosphate | 432.0 | 44.713 |
| 1-[6-chloro-1-(ethylpropyl)-2-hydroxyimidazo[4,5-b]pyridin-7-yl]-4-(methylsulfonyl)benzene | 394.0 | 45.324 |
| 1-((1R)-2-amino-1-ethylethyl)-6-chloro-7-(4-fluorophenyl)imidazo[4,5-b]pyridin-2-ol | 335.0 | 46.969 |
| 1-((1S)-1-ethyl-2-hydroxyethyl)-6-chloro-7-(4-methoxyphenyl)imidazo[4,5-b]pyridin-2-ol | 346.0 | 5.251 |
| 6-chloro-1-(ethylpropyl)-7-(1-methyl(1H-indazol-5-yl))imidazo[4,5-b]pyridin-2-ol | 370.1 | 5.365 |
| 6-chloro-1-(ethylpropyl)-7-(5-methyl(2-pyridyl))imidazo[4,5-b]pyridin-2-ol | 331.0 | 5.708 |
| 6-chloro-1-(ethylpropyl)-7-(2-methyl(1,2,3,4-tetraazol-5-yl))imidazo[4,5-b]pyridin-2-ol | 322.1 | 6.404 |

-continued

| Name | M/Z (M + H unless noted) | AC1.4 Median |
|---|---|---|
| 1-((1S)-1-ethyl-2-hydroxy-2-methylpropyl)-6-chloro-7-(5-fluoro(2-pyridyl))imidazo[4,5-b]pyridin-2-ol | 410.0 | 6.420 |
| (2S)-2-[7-(3,4-difluorophenyl)-6-chloro-2-hydroxyimidazo[4,5-b]pyridinyl]butyl (2S)-2-amino-3-methylbutanoate | 453.1 | 6.640 |
| 6-chloro-7-(4-fluorophenyl)-1-(3-hydroxypropyl)imidazo[4,5-b]pyridin-2-ol | 320.0 | 7.015 |
| 1-((1S)-1-ethyl-2-hydroxyethyl)-6-chloro-7-(5-fluoro(2-pyridyl))imidazo[4,5-b]pyridin-2-ol | 337.0 | 7.549 |
| 1-((1R)-1-ethyl-2-hydroxyethyl)-6-chloro-7-(5-fluoro(2-pyridyl))imidazo[4,5-b]pyridin-2-ol | 337.1 | 7.658 |
| 6-chloro-1-(ethylpropyl)-7-(3-pyridyl)imidazo[4,5-b]pyridin-2-ol | 317.0 | 8.030 |
| 6-chloro-1-(ethylpropyl)-7-[3-(methoxymethyl)phenyl]imidazo[4,5-b]pyridin-2-ol | 359.0 | 8.109 |
| 1-((1R)-1-ethyl-2-hydroxy-2-methylpropyl)-6-chloro-7-(5-fluoro(2-pyridyl))imidazo[4,5-b]pyridin-2-ol | 410.0 | 8.386 |
| 1-((1S)-1-ethyl-2-hydroxyethyl)-6-chloro-7-(5-chloro(2-pyridyl))imidazo[4,5-b]pyridin-2-ol | 353.0 | 9.592 |
| methyl 3-[6-chloro-1-(ethylpropyl)-2-hydroxyimidazo[4,5-b]pyridin-7-yl]benzoate | 372.0 [M − H] | 9.682 |
| 4-(6-chloro-2-hydroxy-1-(pentan-3-yl)-1H-imidazo[4,5-b]pyridin-7-yl)picolinonitrile | 342.1 | 9.842 |
| N-{(2S)-2-[6-chloro-7-(4-fluorophenyl)-2-hydroxyimidazo[4,5-b]pyridinyl]butyl}acetamide | 376 | 8.4925 |
| 1-((1S)-2-amino-1-ethylethyl)-6-chloro-7-(4-fluorophenyl)imidazo[4,5-b]pyridin-2-ol | 334 | 24.3174 |
| 1-((1S)-2-amino-1-ethylethyl)-6-chloro-7-(5-fluoro(2-pyridyl))imidazo[4,5-b]pyridin-2-ol | 335 | |
| N-{(2R)-2-[6-chloro-7-(4-fluorophenyl)-2-hydroxyimidazo[4,5-b]pyridinyl]butyl}acetamide | 377 | 15.6039 |
| 1-((1S)-1-ethyl-3-hydroxy-3-methylbutyl)-6-chloro-7-(4-fluorophenyl)imidazo[4,5-b]pyridin-2-ol | 379 | 1.0092 |
| 1-((1R)-1-ethyl-3-hydroxy-3-methylbutyl)-6-chloro-7-(4-fluorophenyl)imidazo[4,5-b]pyridin-2-ol | 379 | 2.9192 |
| 6-chloro-1-(ethylpropyl)-7-pyrazolylimidazo[4,5-b]pyridin-2-ol | 305 [M + H] 305 [M + H] 306 [M + H] | 0.3235 |
| 2-{(1S)-1-[6-chloro-7-(4-fluorophenyl)-2-hydroxyimidazo[4,5-b]pyridinyl]propyl}propane-1,3-diol | 380 | 4.6812 |
| 6-chloro-1-(methylethyl)-7-pyrazolylimidazo[4,5-b]pyridin-2-ol | 278 | 2.0829 |
| 1-((1S)-1-ethyl-2-hydroxyethyl)-6-chloro-7-pyrazolylimidazo[4,5-b]pyridin-2-ol | 307 | 7.2481 |
| 6-chloro-1-(ethylpropyl)-7-(1-methylpyrazol-3-yl)imidazo[4,5-b]pyridin-2-ol | 320.1 | 1.7950 |
| 1-((1S)-1-methylpropyl)-6-chloroimidazo[4,5-b]pyridin-2-ol | 226.10 | 1.7291 |
| 1-((1R)-1-methylpropyl)-6-chloro-7-pyrazolylimidazo[4,5-b]pyridin-2-ol | M + H = 292.10 292.2 (m + 1) MS (m/z): 292.1 (M + H) | 0.5583 |
| 1-((1S)-1-methylpropyl)-6-chloro-7-pyrazolylimidazo[4,5-b]pyridin-2-ol | 292.10 | 1.0174 |
| 6-chloro-1-[2-methoxy-1-(methoxymethyl)ethyl]-7-pyrazolylimidazo[4,5-b]pyridin-2-ol | 338.1 | 27.9068 |
| 6-chloro-1-(ethylpropyl)-7-imidazolylimidazo[4,5-b]pyridin-2-ol | 305 | 22.2909 |
| 1-((1R)-1-methylpropyl)-7-pyrazolylimidazo[4,5-b]pyridin-2-ol | 258.1 | 18.6973 |
| 6-chloro-1-(methylpropyl)-7-pyrazolylimidazo[4,5-b]pyridin-2-ol | 292.0 | 1.3927 |

†Mean value.

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. At least one chemical entity selected from compounds of Formula I:

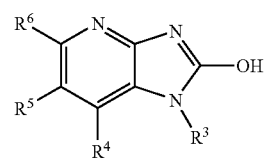

Formula I or a pharmaceutically acceptable salt or tautomer thereof, wherein

R$^3$ is selected from optionally substituted alkyl, optionally substituted cycloalkyl, optionally substituted aryl, optionally substituted heteroaryl, and optionally substituted heterocycloalkyl;

R$^4$ is optionally substituted heteroaryl;

R$^5$ is selected from hydrogen, halo, hydroxy, optionally substituted alkyl, optionally substituted amino, optionally substituted alkenyl, optionally substituted alkynyl, optionally substituted cycloalkyl, optionally substituted aryl, optionally substituted heteroaryl, optionally substituted alkoxy, sulfanyl, and sulfinyl; and R$^6$ is selected from hydrogen, halo, hydroxy, lower alkyl, and lower haloalkyl.

2. At least one chemical entity of claim 1 wherein R$^4$ is selected from optionally substituted oxadiazolyl, optionally substituted pyrazolyl, optionally substituted indazolyl, optionally substituted benzimidazolyl, optionally substituted tetrazolyl, and optionally substituted pyridyl.

3. At least one chemical entity of claim 2 wherein R$^4$ is selected from optionally substituted pyrid-2-yl and optionally substituted pyrid-4-yl.

4. At least one chemical entity of claim 3 wherein R$^4$ is selected from pyrid-2-yl and pyrid-4-yl, each of which is optionally substituted with one or two groups independently chosen from optionally substituted lower alkyl, halo, cyano, sulfonyl, optionally substituted lower alkoxy, aminocarbonyl, optionally substituted amino, alkoxycarbonyl, and acyl.

5. At least one chemical entity of claim 2 wherein R$^4$ is optionally substituted pyrazolyl.

6. At least one chemical entity of claim 5 wherein R$^4$ is pyrazol-1-yl or pyrazol-3-yl, each of which is optionally substituted with one or two groups independently chosen from lower alkyl, halo, and lower alkoxy.

7. At least one chemical entity of claim 6 wherein R$^4$ is pyrazol-1-yl.

8. At least one chemical entity of claim 1 wherein R$^6$ is selected from hydrogen, halo, and lower alkyl.

9. At least one chemical entity of claim 8 wherein R$^6$ is hydrogen.

10. At least one chemical entity of claim 1 wherein R$^5$ is selected from hydrogen, halo, optionally substituted alkenyl, optionally substituted alkynyl, optionally substituted alkyl, optionally substituted amino, optionally substituted alkoxy, and sulfanyl.

11. At least one chemical entity of claim 10 wherein R$^5$ is selected from hydrogen, halo, and optionally substituted alkynyl.

12. At least one chemical entity of claim 11 wherein R$^5$ is selected from hydrogen, fluoro, chloro, and bromo.

13. At least one chemical entity of claim 12 wherein R$^5$ is chloro.

14. At least one chemical entity of claim 12 wherein R$^3$ is selected from optionally substituted heterocycloalkyl, optionally substituted cycloalkyl, and optionally substituted lower alkyl.

15. At least one chemical entity of claim 14 wherein R$^3$ is lower alkyl optionally substituted with one or more groups chosen from optionally substituted phenyl, hydroxy, optionally substituted alkoxy, optionally substituted amino, optionally substituted heteroaryl, halo, and optionally substituted heterocycloalkyl.

16. At least one chemical entity of claim 15 wherein R$^3$ is selected from alkenyl, pentyl, cyclopropyl, butyl, propyl, ethyl, and methyl, each of which is optionally substituted with one or more groups chosen from optionally substituted phenyl, hydroxy, optionally substituted alkoxy, optionally substituted amino, and optionally substituted heterocycloalkyl.

17. At least one chemical entity of claim 16 wherein R$^3$ is selected from 3-pentyl, isopropyl, tert-butyl, 1-ethyl-2-hydroxyethyl, 1-ethyl-2-hydroxyethyl, 1-methyl-2-hydroxethyl, 1-methyl-2-hydroxethyl, 1-methyl-2-hydroxyethyl, 1-ethyl-3-hydroxypropyl, 1-hydroxymethylpropyl, 3-hydroxypropyl, 2-hydroxyethyl, isopropyl, 1-hydroxymethyl-3-methylbutyl, 1-(methoxymethyl)propyl, 1-ethyl-2-hydroxy-2-methylpropyl, 2-hydroxy-tert-buyl, 1-ethyl-2-hydroxy-2-methylpropyl, and 2-hydroxy-1-(2-methylpropyl)ethyl.

18. At least one chemical entity of claim 17 wherein R$^3$ is selected from 3-pentyl, isopropyl, 1-ethyl-2-hydroxyethyl, 1-methyl-2-hydroxethyl, tert-butyl, 1-ethyl-3-hydroxypropyl, 1-hydroxymethyl-3-methylbutyl, 1-(methoxymethyl)propyl, 1-ethyl-2-hydroxy-2-methylpropyl, 2-hydroxy-tert-butyl, and (S)-1-hydroxy-pentan-3-yl, and (S)-1-hydroxy-butan-2-yl.

19. At least one chemical entity of claim 18 wherein R$^3$ is selected from 3-pentyl, isopropyl, (S)-1-hydroxy-pentan-3-yl, and (S)-1-hydroxy-butan-2-yl.

20. At least one chemical entity of claim 16 wherein R$^3$ is 1-methylpropyl.

21. At least one chemical of claim 1 wherein the compound of Formula I is chosen from:

6-chloro-1-(ethylpropyl)-7-(4-pyridyl)imidazo[4,5-b]pyridin-2-ol;
6-chloro-1-(ethylpropyl)-7-(3-pyridyl)imidazo[4,5-b]pyridin-2-ol;
6-chloro-1-(ethylpropyl)-7-(6-(methoxy(3-pyridyl))imidazo[4,5-b]pyridin 2-ol;
6-chloro-1-(ethylpropyl)-7-(2-pyridyl)imidazol[4,5-b]pyridin-2-ol;
6-chloro-1-(ethylpropyl)-7-(2-methoxy(4-pyridyl))imidazo[4,5-b]pyridin-2-ol;
6-chloro-1-(ethylpropyl)-7-(5-methoxy(3-pyridyl))imidazo[4,5-b]pyridin-2-ol;
6-chloro-1-(ethylpropyl)-7-(2-methoxy(4-pyridyl))imidazo[4,5-b]pyridin-2-ol;
4-(6-chloro-2-hydroxy-1-(pentan-3-yl)-1H-imidazo[4,5-b]pyridin-7-yl)picolinonitrile;
6-chloro-1-(ethylpropyl)-7-(6-methoxy(2-pyridyl))imidazo[4,5-b]pyridin-2-ol;
6-chloro-1-(ethylpropyl)-7-(5-hydroxy(3-pyridyl))imidazo[4,5-b]pyridin-2-ol;
6-chloro-7-(5-chloro(3-pyridyl))-1-(ethylpropyl)imidazo[4,5-b]pyridin-2-ol;
6-chloro-1-(ethylpropyl)-7-(6-methyl(2-pyridyl))imidazo[4,5-b]pyridin-2-ol;
6-chloro-1-(ethylpropyl)-7-(4-methyl(2-pyridyl))imidazo[4,5-b]pyridin-2-ol;
6-chloro-1-(ethylpropyl)-7-(5-methyl(2-pyridyl))imidazo[4,5-b]pyridin-2-ol;

6-chloro-1-(ethylpropyl)-7-(6-methyl(3-pyridyl))imidazo[4,5-b]pyridin-2-ol;
6-chloro-1-(ethylpropyl)-7-[2-trifluoromethyl)(4-pyridyl)]imidazo[4,5-b]pyridin-2-ol;
6-chloro-7-(3-chloro(4-pyridyl))-1-(ethylpropyl)imidazo[4,5-b]pyridin-2-ol;
6-chloro-1-(ethylpropyl)-7-(5-fluoro(3-pyridyl))imidazo[4,5-b]pyridin-2-ol;
6-chloro-1-(ethylpropyl)-7-(5-fluoro(2-pyridyl))imidazo[4,5-b]pyridin-2-ol;
6-chloro-1-(ethylpropyl)-7-(3-fluoro(4-pyridyl))imidazo[4,5-b]pyridin-2-ol;
6-chloro-7-(5-chloro(2-pyridyl))-1-(methylethyl)imidazo[4,5-b]pyridin-2-ol;
6-chloro-7-(5-chloro(2-pyridyl))-1-(ethylpropyl)imidazo[4,5-b]pyridin-2-ol;
1-((1S)-1-ethyl-2-hydroxyethyl)-6-chloro-7-(5-chloro(2-pyridyl))imidazo[4,5-b]pyridin-2-ol;
6-chloro-7-(5-fluoro(2-pyridyl))-1-(methylethyl)imidazo[4,5-b]pyridin-2-ol;
6-[6-chloro-1-(ethylpropyl)-2-hydroxyimidazo[4,5-b]pyridin-7-yl]pyridine-3-carbonitrile;
6-[1-((1S)-1-ethyl-2-hydroxyethyl)-6-chloro-2-hydroxyimidazo[4,5-b]pyridin-7-yl]pyridine-3-carbonitrile;
1-[(1R)-1-(methoxymethyl)propyl]-6-chloro-7-(5-fluoro(2-pyridyl))imidazo[4,5-b]pyridin-2-ol; 1-((1R)-1-ethyl-2-hydroxyethyl)-6-chloro-7-(5-fluoro(2-pyridyl))imidazo[4,5-b]pyridin-2-ol;
1-((1R)-1-ethyl-2-hydroxy-2-methylpropyl)-6-chloro-7-(5-fluoro(2-pyridyl))imidazo[4,5-b]pyridin-2-ol; 1-[(1S)-1-(methoxymethyl)propyl]-6-chloro-7-(5-fluoro(2-pyridyl))imidazo[4,5-b]pyridin-2-ol; 1-((1S)-1-ethyl-2-hydroxy-2-methylpropyl)-6-chloro-7-(5-fluoro(2-pyridyl))imidazo[4,5-b]pyridin-2-ol;
1-((1R)-2-amino-1-ethylethyl)-6-chloro-7-(5-fluoro(2-pyridyl))imidazo[4,5-b]pyridin-2-ol; and
1-((1S)-2-amino-1-ethylethyl)-6-chloro-7-[(5-fluoro(2-pyridyl)]imidazo[4,5-b]pyridin-2-ol,
or a pharmaceutically acceptable salt or tautomer thereof.

22. At least one chemical of claim 1 wherein the compound of Formula I is chosen from:
6-chloro-1-(ethylpropyl)-7-pyrazolylimidazo[4,5-b]pyridin-2-ol;
6-chloro-1-(methylethyl)-7-pyrazolylimidazo[4,5-b]pyridin-2-ol;
1-((1S)-1-ethyl-2-hydroxyethyl)-6-chloro-7-pyrazolylimidazo[4,5-b]pyridin-2-ol;
1-((1R)-1-methylpropyl)-6-chloro-7-pyrazolylimidazo[4,5-b]pyridin-2-ol;
1-((1S)-1-methylpropyl)-6-chloro-7-pyrazolylimidazo[4,5-b]pyridin-2-ol;
6-chloro-1-[2-methoxy-1-(methoxymethyl)ethyl]-7-pyrazolylimidazo[4,5-b]pyridin-2-ol;
6-chloro-1-(methylpropyl)-7-pyrazolylimidazo[4,5-b]pyridin-2-ol;
6-chloro-1-(ethylpropyl)-7-(1-methylpyrazol-4-yl)imidazo[4,5-b]pyridin-2-ol;
6-chloro-1-(ethylpropyl)-7-pyrazol-3-ylimidazo[4,5-b]pyridin-2-ol;
6-chloro-1-(ethylpropyl)-7-pyrazol-4-ylimidazo[4,5-b]pyridin-2-ol; and
6-chloro-1-(ethylpropyl)-7-(1-methylpyrazol-3-yl)imidazo[4,5-b]pyridin-2-ol,
or a pharmaceutically acceptable salt or tautomer thereof.

23. A pharmaceutically acceptable composition comprising a pharmaceutically acceptable carrier and at least one chemical entity of claim 1.

24. A pharmaceutical composition of claim 23, wherein the composition is formulated in a form chosen from a tablet, capsule, powder, liquid suspension, suppository and aerosol.

25. At least one chemical entity of claim 1 wherein the compound of Formula I is chosen from:
6-chloro-1-(ethylpropyl)-7-indol-4-ylimidazo[4,5-b]pyridin-2-ol;
7-(1H-indazol-5-yl)-6-chloro-1-(ethylpropyl)imidazo[4,5-b]pyridin-2-ol;
7-(1H-indazol-6-yl)-6-chloro-1-(ethylpropyl)imidazo[4,5-b]pyridin-2-ol;
6-chloro-1-(ethylpropyl)-7-(1-methyl(1H-indazol-5-yl))imidazo[4,5-b]pyridin-2-ol; and
6-chloro-1-(ethylpropyl)-7-(1-methyl(1H-indazol-6-yl))imidazo[4,5-b]pyridin-2-ol,
or a pharmaceutically acceptable salt or tautomer thereof.

26. At least one chemical entity of claim 1 wherein the compound of Formula I is chosen from:
6-chloro-1-(ethylpropyl)-7-(2-thienyl)imidazo[4,5-b]pyridin-2-ol;
6-chloro-1-(ethylpropyl)-7-(3-thienyl)imidazo[4,5-b]pyridin-2-ol;
6-chloro-7-(5-chloro(2-thienyl))-1-(ethylpropyl)imidazo[4,5-b]pyridin-2-ol;
1-((1S)-1-ethyl-2-hydroxyethyl)-6-chloro-7-(2-thienyl)imidazo[4,5-b]pyridin-2-ol;
1-((1S)-1-ethyl-2-hydroxyethyl)-6-chloro-7-(3-thienyl)imidazo[4,5-b]pyridin-2-ol; and
1-((1S)-1-ethyl-2-hydroxyethyl)-6-chloro-7-(5-chloro(2-thienyl))imidazo[4,5-b]pyridin-2-ol,
or a pharmaceutically acceptable salt or tautomer thereof.

27. At least one chemical of claim 1 wherein the compound of Formula I is chosen from:
7-(2H-1,2,3,4-tetraazol-5-yl)-6-chloro-1-(ethylpropyl)imidazo[4,5-b]pyridin-2-ol;
6-chloro-1-(ethylpropyl)-7-(2-methyl(1,2,3,4-tetraazol-5-yl))imidazo[4,5-b]pyridin-2-ol;
6-chloro-1-(ethylpropyl)-7-(5-methyl(1,2,4-oxadiazol-3-yl))imidazo[4,5-b]pyridin-2-ol;
6-chloro-1-(ethylpropyl)-7-pyrimidin-5-ylimidazo[4,5-b]pyridin-2-ol;
6-chloro-1-(ethylpropyl)-7-(5-methylpyrimidin-2-yl)imidazo[4,5-b]pyridin-2-ol;
1-((1S)-1-ethyl-2-hydroxyethyl)-6-chloro-7-pyrazin-2-ylimidazo[4,5-b]pyridin-2-ol;
6-chloro-1-(ethylpropyl)-7-imidazolylimidazo[4,5-b]pyridin-2-ol; and
1-((1R)-1-methylpropyl)-7-pyrazolylimidazo[4,5-b]pyridin-2-ol,
or a pharmaceutically acceptable salt or tautomer thereof.

28. At least one chemical entity of claim 2 wherein $R^6$ is selected from hydrogen, halo and lower alkyl.

29. At least one chemical entity of claim 28 wherein $R^6$ is hydrogen.

30. At least one chemical entity of claim 29 wherein $R^5$ is selected from hydrogen, halo and lower alkyl.

31. At least one chemical entity of claim 30 wherein $R^5$ is selected from hydrogen and chloro.

32. At least one chemical entity of claim 31 wherein $R^5$ is chloro.

33. At least one chemical entity of claim 32 wherein $R^3$ is selected from isopropyl, 1-methylpropyl, (R)-1-methylpropyl, (S)-1-methylpropyl, 3-pentyl, 1-ethyl-2-hydroxyethyl, (R)-1-ethyl-2-hydroxyethyl and (S)-1-ethyl-2-hydroxyethyl.

34. At least one chemical entity of claim 33 wherein $R^4$ is selected from pyrid-2-yl and pyrid-4-yl, each of which is optionally substituted with one or two groups independently chosen from optionally substituted lower alkyl, halo, cyano, sulfonyl, optionally substituted lower alkoxy, aminocarbonyl, optionally substituted amino, alkoxycarbonyl, and acyl.

35. At least one chemical entity of claim 33 wherein $R^4$ is selected from pyrazol-1-yl and pyrazol-3-yl, each of which is optionally substituted with one or two groups independently chosen from lower alkyl, halo, and lower alkoxy.

36. At least one chemical entity of claim 33 wherein $R^4$ is pyrazol-1-yl.

37. At least one chemical entity of claim 33 wherein $R^4$ is selected from thien-2-yl and thien-3-yl, each of which is optionally substituted with one or two groups independently chosen from lower alkyl, halo, and lower alkoxy.

38. At least one chemical entity of claim 16 wherein $R^3$ is selected from isopropyl, 1-methylpropyl, (R)-1-methylpropyl, (S)-1-methylpropyl, 3-pentyl, 1-ethyl-2-hydroxyethyl, (R)-1 and (S)-1-ethyl-2-hydroxyethyl.

* * * * *